United States Patent
Li et al.

(10) Patent No.: US 10,239,851 B2
(45) Date of Patent: Mar. 26, 2019

(54) CARBOXYLIC ACID DERIVATIVES AND USE THEREOF IN THE PREPARATION OF PRODRUGS

(71) Applicant: Qingeng Li, Chongqing (CN)

(72) Inventors: Qingeng Li, Chongqing (CN); Tao Wang, Chongqing (CN); Gang Chen, Chongqing (CN); Yuanzhong Wang, Chongqing (CN); Wei Mao, Chongqing (CN); Tong Wu, Chongqing (CN); Lingguo Zeng, Chongqing (CN)

(73) Assignee: Qingeng Li, Chongqing (CN)

( * ) Notice: Subject to any disclaimer, the term of this patent is extended or adjusted under 35 U.S.C. 154(b) by 0 days.

(21) Appl. No.: 15/119,587

(22) PCT Filed: Feb. 16, 2015

(86) PCT No.: PCT/CN2015/073165
§ 371 (c)(1),
(2) Date: Aug. 17, 2016

(87) PCT Pub. No.: WO2015/120820
PCT Pub. Date: Aug. 20, 2015

(65) Prior Publication Data
US 2017/0057939 A1    Mar. 2, 2017

(30) Foreign Application Priority Data

Feb. 17, 2014  (CN) .......................... 2014 1 0053129
Apr. 17, 2014  (CN) .......................... 2014 1 0154956

(51) Int. Cl.
| | |
|---|---|
| *C07C 229/20* | (2006.01) |
| *C07D 305/14* | (2006.01) |
| *C07C 227/04* | (2006.01) |
| *C07C 227/18* | (2006.01) |
| *C07C 229/22* | (2006.01) |
| *C07D 203/02* | (2006.01) |
| *C07D 203/08* | (2006.01) |
| *C07D 295/15* | (2006.01) |
| *C07F 9/09* | (2006.01) |
| *C07F 9/38* | (2006.01) |
| *C07D 405/12* | (2006.01) |
| *C07D 207/06* | (2006.01) |

(52) U.S. Cl.
CPC .......... *C07D 305/14* (2013.01); *C07C 227/04* (2013.01); *C07C 227/18* (2013.01); *C07C 229/20* (2013.01); *C07C 229/22* (2013.01); *C07D 203/02* (2013.01); *C07D 203/08* (2013.01); *C07D 207/06* (2013.01); *C07D 295/15* (2013.01); *C07D 405/12* (2013.01); *C07F 9/091* (2013.01); *C07F 9/3808* (2013.01); *Y02P 20/55* (2015.11)

(58) Field of Classification Search
CPC .................................................. C07C 229/20
See application file for complete search history.

(56) References Cited

FOREIGN PATENT DOCUMENTS

| | | |
|---|---|---|
| CN | 1907945 A | 2/2007 |
| CN | 101094840 A | 12/2010 |
| CN | 101898978 A | 12/2010 |
| CN | 102015621 A | 4/2011 |
| EP | 3109229 A1 | 12/2016 |
| EP | 3109242 A1 | 12/2016 |
| JP | 63079854 | * 4/1988 |
| WO | WO-2004106349 A1 | 12/2004 |

OTHER PUBLICATIONS

CAS Reg. No. 113684-87-0, entered Apr. 2, 1988.*
CAS Reg No. 1556901-43-9, entered into STN on Feb. 26, 2014.*
CAS Reg No. 1384428-87-8, entered into STN on Jul. 26, 2013.*
CAS Reg No. 1346597-54-3, entered into STN on Nov. 30, 2011.*
CAS Reg No. 1346597-49-6, entered into STN on Nov. 30, 2011.*
Takeuchi et al, abstract of CAS Doc No. 109:230305, 1988, p. 1 (Year: 1988).*
"International Application No. PCT/CN2015/073165, International Search Report dated May 28, 2015", w/ English Translation, (May 28, 2015), 7 pgs.
"International Application No. PCT/CN2015/073165, Written Opinion dated May 28, 2015", (May 28, 2015), 4 pgs.
Desmoulin, Franck, et al., "Metabolism of capecitabine, an oral fluorouracil prodrug: 19F NMR studies in animal models and human urine", Drug metabolism and disposition 30.11, (2002), 1221-1229.

(Continued)

*Primary Examiner* — Rebecca L Anderson
*Assistant Examiner* — Karen Cheng
(74) *Attorney, Agent, or Firm* — Schwegman Lundberg & Woessner, P.A.

(57) ABSTRACT

The present invention discloses a class of carboxylic acid derivatives and use thereof in preparation of prodrugs. The carboxylic acid derivatives have the general formula (I), wherein $R^1$ is H or alkyl; X is H or F; Y is F or fluoroalkyl; n is 0, 1, 2, 3, 4, 5, or 6; W is $W^1$ or $W^2$; $W^1$ is $NR^2R^3$, $NR^2R^3.A$,

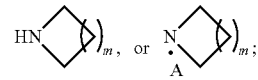

$R^2$ and $R^3$ are each independently H, alkyl, cycloalkyl, or a protecting group for amino; m is 0, 1, 2, or 3; A is an acid; $W^2$ is $COOR^4$, $OPO(OR^4)_2$, or $PO(OR)_2$; $R^4$ is H, or a protecting group for carboxyl or hydroxyl in phosphoric acid.

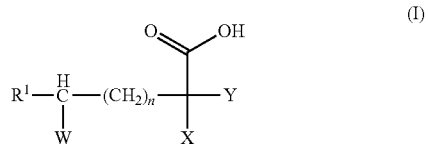

13 Claims, 3 Drawing Sheets

(56) References Cited

OTHER PUBLICATIONS

Jurcík, Václav, et al., "Single enantiomer synthesis of a-(trifluoromethyl)-ß-lactam", Beilstein journal of organic chemistry 7.1, (2011), 759-766.

"Chinese Application No. 201580008927.2, Office Action dated Mar. 28, 2017", w/ English Translation, (Mar. 28, 2017), 14 pgs.

Hook, David F., et al., "Probing the Proteolytic Stability of ß-Peptides Containing a-Fluoro-and a-Hydroxy-ß-Amino Acids", ChemBioChem 5.5, (2004), 691-706.

"Accela Chembio Inc.: "1346597-49-6"", Chemical Catalog, (Nov. 30, 2011), pp. 1-1, XP055465699.

"Accela Chembio Inc.: "1346597-54-3"", Chemical Catalog, (Nov. 30, 2011), pp. 1-1, XP055465700.

"Chinese Application Serial No. 201580008927.2, Office Action dated Mar. 28, 2018", (Mar. 28, 2018), 8 pgs.

"Chinese Application Serial No. 201580008927.2, Office Action dated Dec. 19, 2017", w/ English Translation, (Dec. 19, 2017), 7 pgs.

"European Application Serial No. 15 748 471.8 Extended European Search Report dated Oct. 7, 2017", (Oct. 7, 2017), 13 pgs.

"European Application Serial No. 15 748 471.8 Office Action dated Apr. 18, 2018", (Apr. 18, 2018), 4 pgs.

Barney, A. L., et al., "a, a-Difluoroglutaric Acid", Journal of the American Chemical Society 72.7, (1950), 3193-3194.

Pattison, F. L.M., et al., "The synthesis of a-monofluoroalkanoic acids", Canadian Journal of Chemistry 43.6, (1965), 1700-1713.

Takeuchi, Yoshio, et al., "The first versatile and practical building blocks equivalent to the synthon of monofluoromethylene dicarbanion", The Journal of Organic Chemistry 52.22, (1987), 5061-5063.

\* cited by examiner

CARBOXYLIC ACID DERIVATIVES AND USE THEREOF IN THE PREPARATION OF PRODRUGS

CROSS-REFERENCE TO RELATED APPLICATIONS

The present application is a U.S. National Stage Filing under 35 U.S.C. 371 from International Application No. PCT/CN2015/073165, filed on Feb. 16, 2015, and published as WO 2015/120820 on Aug. 20, 2015, which claims the benefit of priority from Chinese patent application No. 201410053129.9 filed on Feb. 17, 2014 and Chinese patent application No. 201410154956.7 filed on Apr. 17, 2014, the contents of which are incorporated herein by reference.

TECHNICAL FIELD

The present invention relates to the field of pharmacy, specifically to carboxylic acid derivatives and use thereof in the preparation of prodrugs.

BACKGROUND ART

A prodrug, also referred to as a precursor of a drug, refers to a compound which achieves pharmacological action after the conversion in an organism. A prodrug per se has no or little bioactivity, and releases an active agent after metabolism in vivo. The purpose of investigating and preparing a prodrug is to increase the bioavailability, modify the solubility, enhance the targeting properties, or reduce the toxicity or side effects of the parent drug. It is advantageous for many drugs, especially those having low bioavailability, poor water solubility or high toxic side effects, to be prepared into prodrugs.

In general, it is required in clinic that a prodrug can be quickly dissociated into a ligand and a parent drug after entering the body, and the ligand is non-toxic. The parent drug thus released can exert pharmaceutical effects, and the non-toxic ligand is of no harm to the body.

However, it is very difficult to achieve such a purpose. For example, fospropofol disodium marketed in the US in 2008 is a prodrug of propofol, which has the following metabolism in vivo:

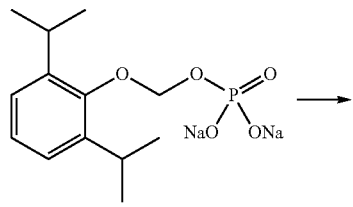

Fospropofol disodium

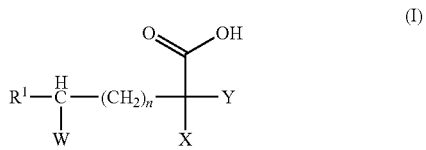

Although fospropofol addresses the problem of poor water solubility of propofol, it can be seen from the above scheme that the metabolism of fospropofol in vivo would result in production of formaldehyde having high toxicity, which would cause unnecessary harm to patients. In addition, according to the published data (as shown below), fospropofol is significantly higher in dosage and is much longer in latent period and persistent period, in comparison to propofol.

| Name of Drug | Dosage (mg/kg) | Latent Period (s) | Persistent period (s) | Data Sources |
|---|---|---|---|---|
| Propofol | 15 (1.25 * $ED_{50}$) | 10.7 | No Report | Br. J. Anaesth. (1980), 52, 731 (mice) |
|  | 25 (2 * $ED_{50}$) | 8.4 ± 1.1 | 324.8 ± 98.9 | mice, results from the present lab |
| Fospropofol | 85 (1.25 * $ED_{50}$) | 105 | No Report | FDA Application NO. (NDA) 022244 |
|  | 136 (2 * $ED_{50}$) | 81 | 804 | Pharmacology Reviews of Fosproporfol (Part I) page 30-31 (mice) |

This suggests that fospropofol is difficult to dissociate quickly in vivo, and thus is not an ideal prodrug of propofol. A suitable ligand is critical for an ideal prodrug. As such, it is one of the urgent tasks for a skilled artisan in the field of pharmacy to search for good ligands for prodrugs. A "good ligand" should satisfy the following criteria: the prodrug formed from the ligand and a parent drug has improved physicochemical properties or bioavailability, and can quickly release the parent drug after entering the body, and the ligand has no or little toxicity.

SUMMARY OF THE INVENTION

It is one object of the present invention to provide a carboxylic acid derivative as a ligand for a prodrug which has different physicochemical properties from the parent drug and can be quickly dissociated in vivo to release the parent drug, so as to exert effects.

The carboxylic acid derivative of the present invention has following general formula (I):

$$R^1-\underset{W}{\underset{|}{\overset{H}{\underset{|}{C}}}}-(CH_2)_n-\underset{X}{\underset{|}{C}}-Y \quad\quad (I)$$

with $O=C-OH$ on the central carbon.

wherein,
$R^1$ is H or alkyl;
X is H or F;
Y is F or alkyl substituted with one or more fluorine atoms;
n is 0, 1, 2, 3, 4, 5 or 6;
W is $W^1$ or $W^2$;
$W^1$ is $NR^2R^3$, $NR^2R^3 \cdot A$,

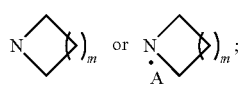

$R^2$, $R^3$ are each independently H, alkyl, cycloalkyl, or a protecting group for amino;

m is 0, 1, 2 or 3;

A is an acid;

$W^2$ is $COOR^4$, $OPO(OR^4)_2$ or $PO(OR^4)_2$;

$R^4$ is H, or a protecting group for carboxyl or hydroxyl in phosphoric acid.

According to an embodiment of the present invention, $R^1$ is H or $C_{1-6}$ alkyl. Preferably, $R^1$ is H, methyl, ethyl, n-propyl or isopropyl.

According to an embodiment of the present invention, Y is F or $C_{1-6}$ alkyl substituted with one or more fluorine atoms. Preferably, Y is F, $CF_3$ or $CHF_2$.

According to an embodiment of the present invention, W is $W^1$.

According to an embodiment of the present invention, $R^2$, $R^3$ are not H at the same time.

According to an embodiment of the present invention, $R^2$ and/or $R^3$ are each independently $C_{1-6}$ alkyl, such as methyl, ethyl, propyl, isopropyl, butyl or isobutyl.

According to an embodiment of the present invention, $R^2$ and/or $R^3$ are each independently $C_{3-6}$ cycloalkyl, such as cyclopropyl, cyclobutyl, cyclopentyl or cyclohexyl.

According to an embodiment of the present invention, $R^2$ and/or $R^3$ are each independently $C_{1-6}$ alkoxycarbonyl optionally substituted with phenyl, such as benzyloxycarbonyl or tert-butyloxycarbonyl.

According to an embodiment of the present invention, $R^2$ and/or $R^3$ are each independently benzyl optionally substituted with one or more halogens. Preferably, $R^2$ and/or $R^3$ are each independently benzyl optionally substituted with one or more fluorine or chlorine atoms, such as benzyl, 3-chlorobenzyl, 4-fluorobenzyl or 2,4-difluorobenzyl.

According to an embodiment of the present invention, $R^2$, $R^3$ are each independently H, methyl, ethyl, n-propyl, isopropyl, cyclopropyl, cyclobutyl, cyclopentyl, cyclohexyl, benzyloxycarbonyl, tert-butyloxycarbonyl, benzyl, 3-chlorobenzyl, 4-fluorobenzyl or 2,4-difluorobenzyl.

According to an embodiment of the present invention, the acid A is an acid which can form a salt with an amine, such as hydrochloric acid, hydrobromic acid, sulfuric acid, phosphoric acid, trifluoroacetic acid, difluoroacetic acid, fluoroacetic acid, acetic acid, benzensulfonic acid or p-toluene sulfonic acid.

According to an embodiment of the present invention, W is $W^2$.

According to an embodiment of the present invention, $R^4$ is $C_{1-6}$ alkyl optionally substituted with one or more phenyls, such as methyl, ethyl, diphenylmethyl, triphenylmethyl or benzyl.

According to an embodiment of the present invention, when X and Y are different (i.e., the α-C of the carboxyl in the carboxylic acid derivative is a chiral atom), the carbon atom to which both X and Y are attached is in a single R configuration, in a single S configuration, or in both R and S configurations.

According to an embodiment of the present invention, a compound of general formula (I) can be converted into a compound of general formula (II) or (III) through conventional chemical means. For example, a compound of general formula (I) can be converted into a corresponding carboxy-late (II) through a neutralization reaction, or into a corresponding acyl halide or a mixed sulfonic anhydride (III) through reacting with a halogenating agent (such as thionyl chloride or phosphorus halide) or sulfonyl chloride.

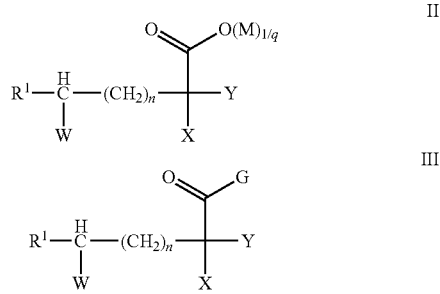

wherein, $R^1$, X, Y, n and W are as defined above for the carboxylic acid derivative of general formula (I);

M is a metal ion;

q is the charge number of M;

G is Cl, Br or benzenesulfonyloxy optionally substituted with alkyl.

According to an embodiment of the present invention, M in the above general formula (II) is an alkali metal ion, such as sodium ion or potassium ion, an alkaline earth metal ion, such as magnesium ion, zinc ion or calcium ion, or a trivalent metal ion, such as aluminum ion or iron ion. More preferably, M is a sodium ion or a potassium ion.

According to an embodiment of the present invention, G in the above general formula (III) is Cl, Br or benzenesulfonyloxy optionally substituted with $C_{1-6}$ alkyl. Preferably, G is Cl, Br,

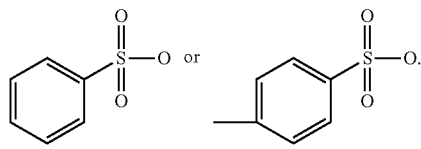

According to an embodiment of the present invention, the carboxylic acid derivative of the present invention is selected from the group consisting of:

4-N,N-dimethylamino-2(R)-fluorobutyric acid hydrochloride;

4-N-isopropylamino-2(R,S)-fluorobutyric acid hydrochloride;

4-N,N-diethylamino-2(R,S)-trifluoromethylbutyric acid hydrochloride;

4-N-benzylamino-2,2-difluorobutyric acid hydrochloride;

4-N-isobutylamino-2(R,S)-difluoromethylbutyric acid hydrochloride;

4-N-(aziridin-1-yl)-2(R,S)-difluoromethylbutyric acid hydrochloride;

4-N-(pyrrolidin-1-yl)-2(R,S)-fluorobutyric acid hydrochloride;

3-N-benzylamino-2(R,S)-(1,1-difluoromethyl)propionic acid hydrochloride;

6-N-cyclohexylamino-2(R,S)-trifluoromethylhexanoic acid hydrochloride;

4-benzyloxy-4-oxo-2(R,S)-fluorobutyric acid;

5-benzyloxy-5-oxo-2(R)-fluoropentanoic acid;

6-benzyloxy-6-oxo-2(S)-fluorohexanoic acid;
dibenzyl [1-(3-(R,S)-fluoro-3-carboxy)propyl] phosphate triester;
dibenzyl [1-(5-(S)-fluoro-5-carboxy)pentyl] phosphate triester;
4-(dibenzyloxy)phosphoryl-2(R,S)-fluorobutyric acid;
5-(dibenzyloxy)phosphoryl-2(R)-fluoropentanoic acid;
4-benzyloxy-4-oxo-2(R,S)-fluorobutyryl chloride;
sodium 5-benzyloxy-5-oxo-2(R)-fluorovalerate;
dibenzyl [1-(3-(R,S)-fluoro-4-oxo-4-chloro)butyl] phosphate triester;
dibenzyl [potassium 1-(4-(S)-fluoro-5-carboxylate)pentyl] phosphate triester;
4-(dibenzyloxy)phosphoryl-2(R,S)-fluorobutyryl chloride;
sodium 4-N,N-dimethylamino-2(R,S)-fluorobutyrate;
calcium 4-N,N-diethylamino-2(R,S)-fluorobutyrate;
aluminum 3-N-benzylamino-2(R,S)-benzyloxypropionate;
4-N,N-dimethylamino-2(R,S)-fluorobutyryl chloride hydrochloride;
4-N-benzylamino-2,2-difluorobutyryl chloride hydrochloride;
4-N,N-dimethylamino-2(R,S)-fluorobutyric acid; and
4-N,N-dimethylamino-2(S)-fluorobutyric acid hydrochloride.

It is another object of the present invention to provide use of a carboxylic acid derivative of the above general formula (I), (II) or (III) in the preparation of a prodrug.

According to an embodiment of the present invention, the prodrug is a prodrug of a propofol drug.

According to an embodiment of the present invention, the prodrug is a prodrug of a taxane drug.

DETAILED DESCRIPTIONS OF THE INVENTION

Definitions

Figure 1:
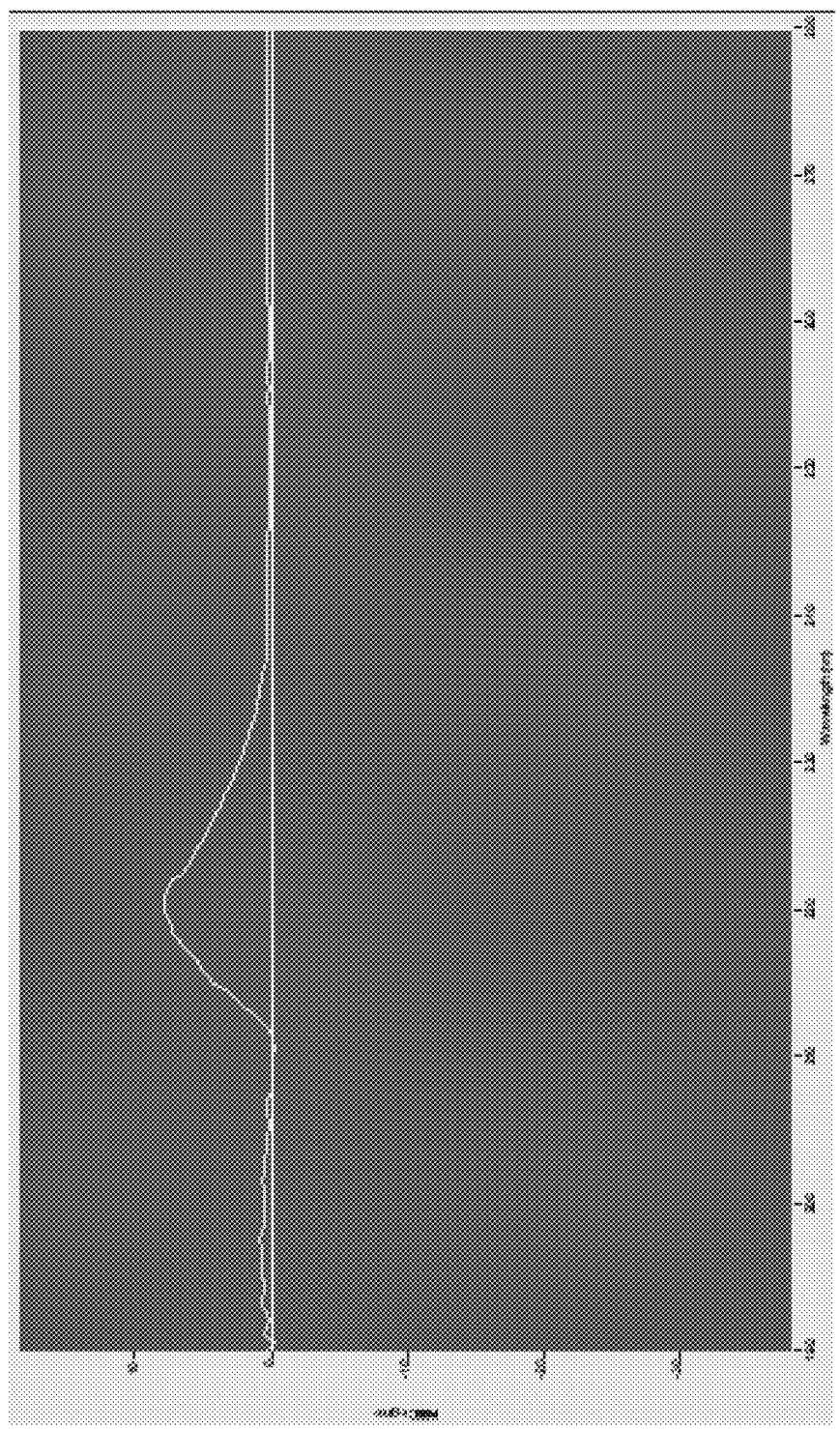
FIG. 1 is a circular dichroism spectra of a compound of formula (VIII).
Figure 2:
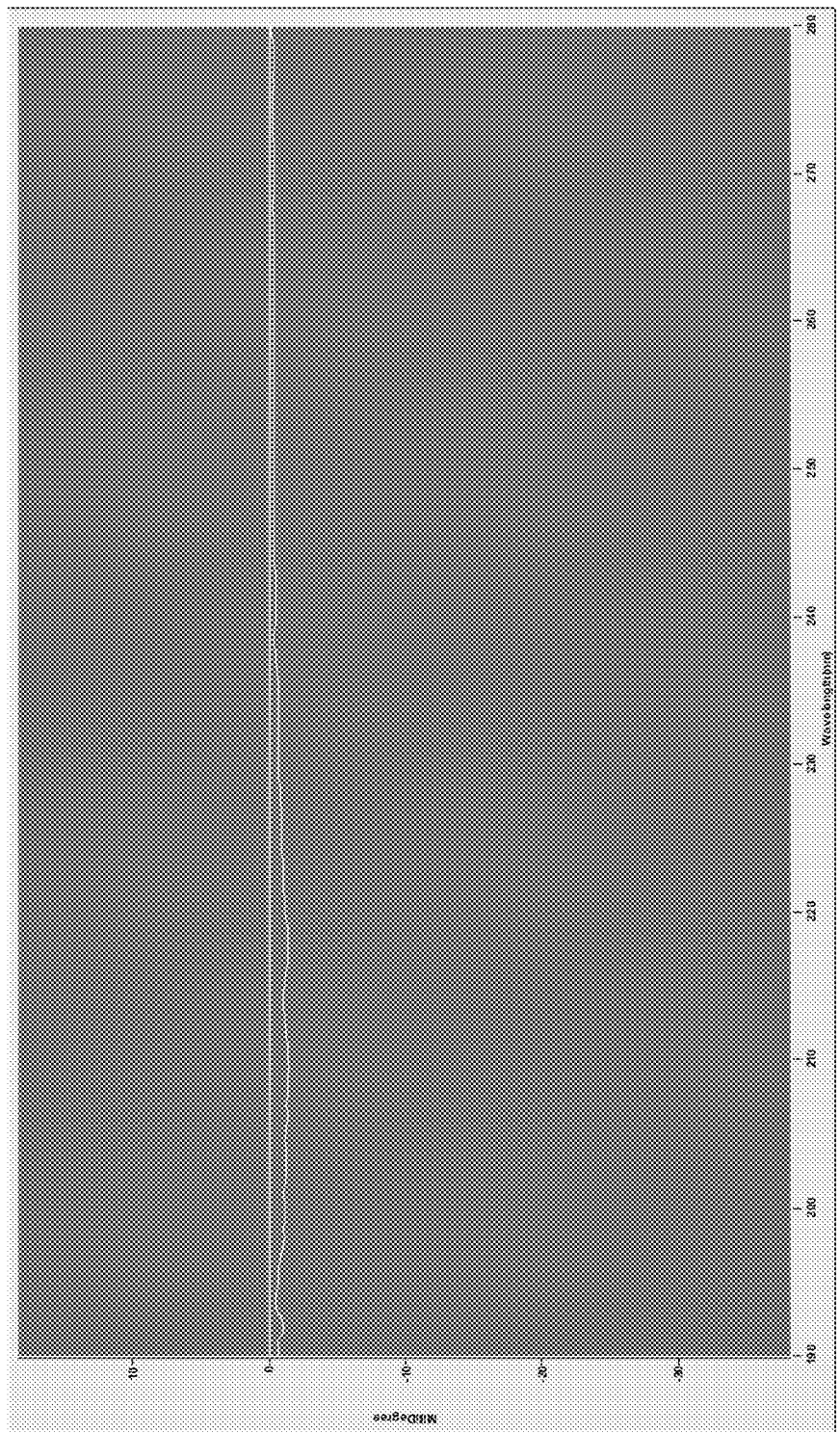
FIG. 2 is a circular dichroism spectra of a compound of formula (IX).
Figure 3:
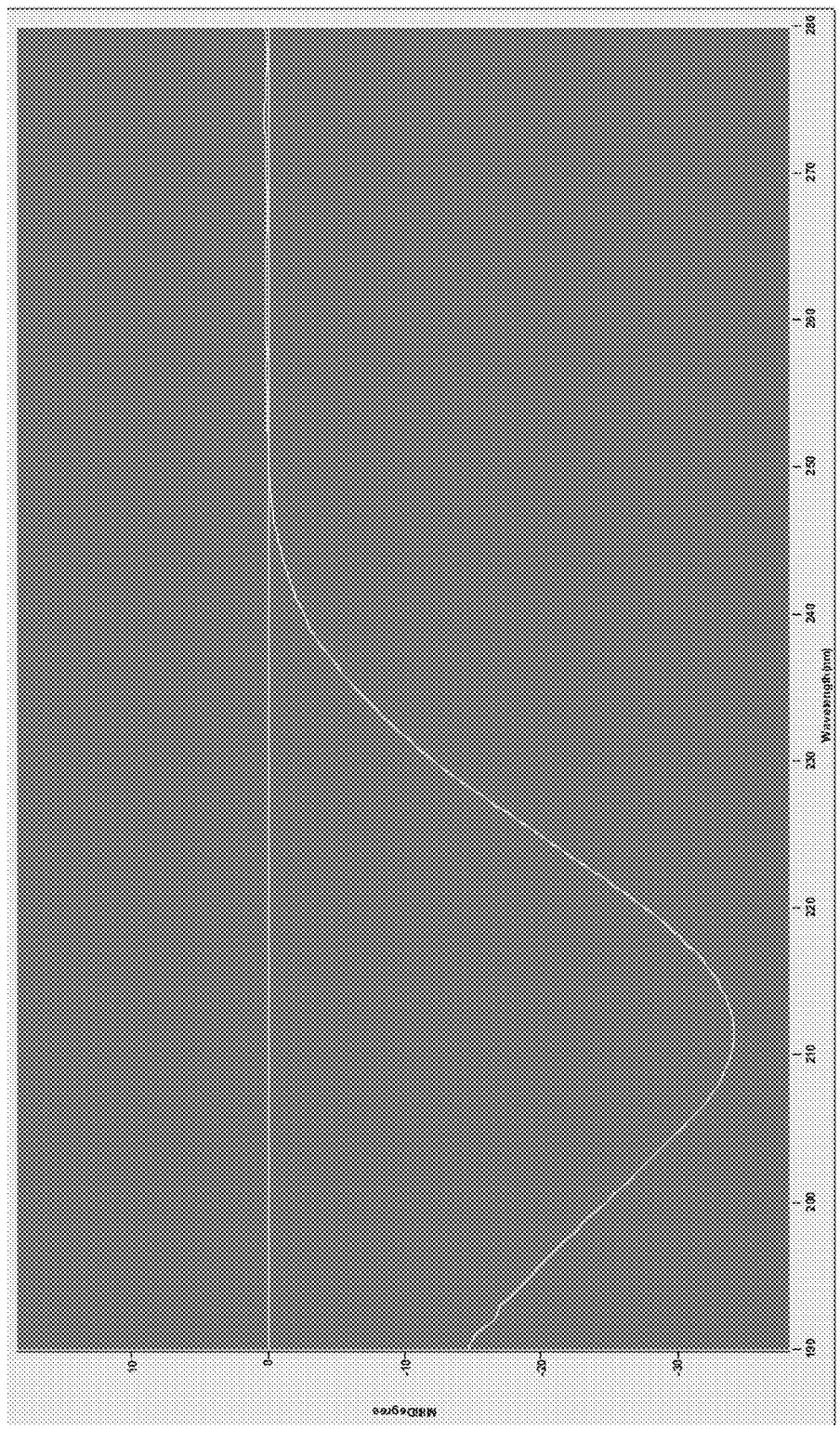
FIG. 3 is a circular dichroism spectra of compound 4-N,N-dimethylamino-2(R)-2-fluorobutyric acid (I') obtained by the hydrolysis of a compound of formula (III').

The term "halogen" as used herein refers to fluorine, chlorine, bromine or iodine, preferably fluorine, chlorine or bromine.

The term "$C_{1-6}$ alkyl" as used herein refers to a saturated, linear or branched hydrocarbon group having 1-6 carbon atoms, such as methyl, ethyl, propyl, isopropyl, n-butyl, isobutyl, sec-butyl, tert-butyl, n-pentyl, isopentyl, neo-pentyl, n-hexyl, isohexyl and the like, preferably methyl, ethyl, propyl, isopropyl, butyl or isobutyl, preferably methyl, ethyl or propyl.

The term "$C_{3-6}$ cycloalkyl" as used herein refers to a saturated monocyclic hydrocarbon group having 3-6 carbon atoms, such as cyclopropyl, cyclobutyl, cyclopentyl or cyclohexyl.

The term "an protecting group for amino" as used herein refers to a protecting group for preventing an amino group from undergoing undesired chemical reactions, including but not limited to an alkoxycarbonyl protecting group, such as methoxycarbonyl, ethoxycarbonyl, propoxycarbonyl, tert-butyloxycarbonyl, benzyloxycarbonyl and the like, and an alkyl protecting group, such as benzyl with or without substitution on the phenyl ring and the like.

The term "a protecting group for carboxyl or hydroxyl in phosphoric acid" as used herein refers to a protecting group for preventing a carboxyl or the hydroxyl group in phosphoric acid from undergoing undesired chemical reactions, including but not limited to methyl, ethyl, propyl, diphenylmethyl, triphenylmethyl, benzyl and the like.

The term "an acid which can form a salt with an amine" as used herein refers to an inorganic or organic acid commonly used in the field of organic chemistry which can form a salt with an amine. The inorganic acid includes, but is not limited to, hydrochloric acid, hydrobromic acid, hydroiodic acid, sulfuric acid, pyrosulfuric acid, phosphoric acid, nitric acid and the like. The organic acid includes, but is not limited to, formic acid, acetic acid, propionic acid, butyric acid, pivalic acid, trifluoroacetic acid, difluoroacetic acid, fluoroacetic acid, acetoacetic acid, benzoic acid, methanesulfonic acid, ethanesulfonic acid, trifluoromethanesulfonic acid, benzensulfonic acid, p-toluene sulfonic acid, naphthalenesulfonic acid, camphorsulfonic acid, and the like.

The term "benzenesulfonyloxy" as used herein refers to a group having a structure of

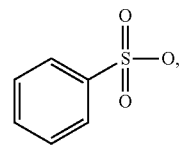

which is linked to the remainder of a molecule via the oxygen atom attached to the sulfur atom through a single bond.

The term "$C_{1-6}$ alkoxycarbonyl" as used herein refers to an alkoxy group linked to the remainder of a molecule via a carbonyl having 1-6 carbon atoms in total, such as methoxycarbonyl, ethoxycarbonyl, propoxycarbonyl, tert-butyloxycarbonyl, pentyloxycarbonyl, etc.

Reaction Scheme

When W is $W^1$, the carboxylic acid derivative of general formula (I) of the present invention can be prepared according to following Reaction Scheme 1:

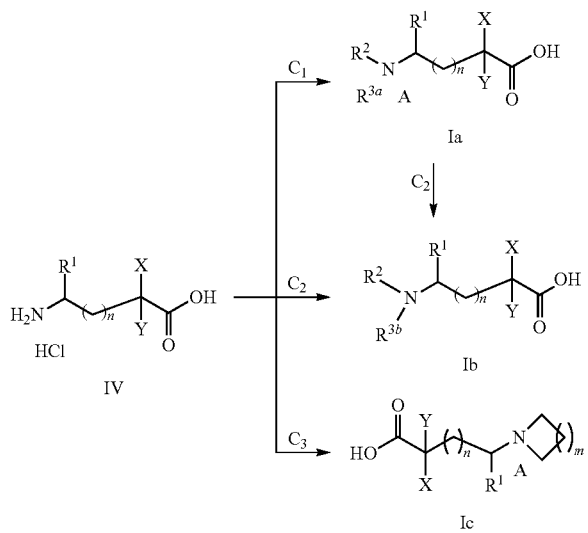

Reaction Scheme 1

In the above Reaction Scheme 1, the compounds of formulae (Ia), (Ib) and (Ic), which all belong to the compound of general formula (I), are obtained by reacting the compound of general formula (IV) with an alkylating agent for amino ($C_1$ or $C_3$) or a protecting agent for amino ($C_2$), wherein, $R^1$, $R^2$, X, Y, n, m, and A are as defined above;

$C_1$ is an alkylating agent for amino, such as formic acid/formaldehyde, dimethyl sulfate, bromoethane, bromopropane, chlorobutane, acetone, butanone, cyclopentanone, cyclohexanone, benzaldehyde and the like;

$C_2$ is a protecting agent for amino, such as benzyl chloroformate, di-tert-butyloxycarbonylcarbonic anhydride, benzyl chloride, benzyl bromide and the like;

$C_3$ is another alkylating agent for amino, such as 1-chloro-2-bromoethane, 1-chloro-4-bromobutane, 1-chloro-5-bromopentane and the like;

$R^{3a}$ is alkyl or cycloalkyl, especially $C_{1-6}$ alkyl, such as methyl, ethyl, propyl, isopropyl, butyl or isobutyl, or $C_{3-6}$ cycloalkyl, e.g., cyclopropyl, cyclobutyl, cyclopentyl or cyclohexyl.

$R^{3b}$ is a protecting group for amino, especially $C_{1-6}$ alkoxycarbonyl optionally substituted with phenyl (such as benzyloxycarbonyl or tert-butyloxycarbonyl) or benzyl optionally substituted with one or more halogen atoms (such as benzyl, 3-chlorobenzyl, 4-fluorobenzyl or 2,4-difluorobenzyl).

When W is $W^2$, the carboxylic acid derivative of general formula (I) of the present invention can be prepared according to following Reaction Scheme 2:

Reaction Scheme 2

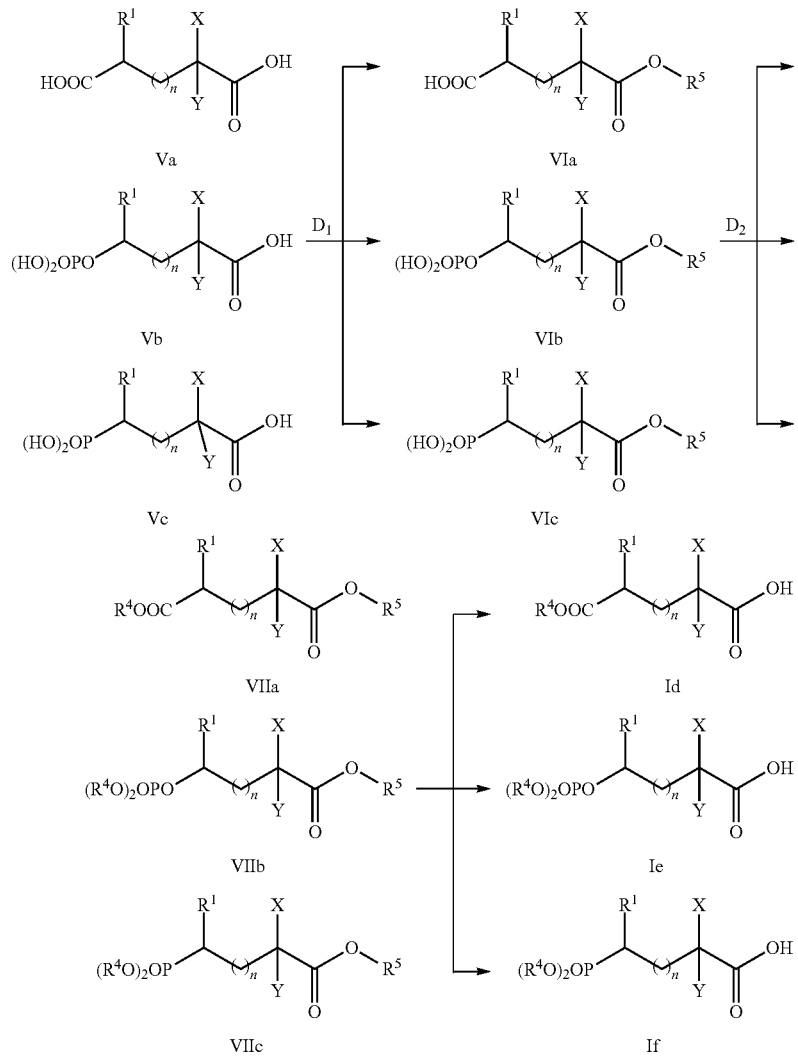

In the above Reaction Scheme 2, the compounds of formulae (Id), (Ie) and (If), which all belong to the compound of general formula (I), are obtained by the following steps: preparing the compounds of formulae (VIa), (VIb) and (VIc) by reacting the compounds of formulae (Va), (Vb) and (Vc) with $D_1$ (a protecting agent for the carboxyl at position 1), respectively, then preparing the compounds of formulae (VIIa), (VIIb) and (VIIc) by protecting the terminal carboxyl or the hydroxyl in the phosphoric acid with the protecting agent $D_2$, and finally preparing the compounds of formulae (Id), (Ie) and (If) by removing $R^5$ (the protecting group for the carboxyl at position 1), wherein, R⁴, X, Y and n are as defined above;

D, the protecting agent for the carboxyl at position 1, is selected from the group consisting of methanol, methanol substituted with silyl, 9-fluorenylmethanol, 2-iodo-2-methylpropane, benzyl halide and the like;

D$_2$, the protecting agent for the terminal carboxyl or the hydroxyl in the phosphoric acid, is selected from the group consisting of iodomethane, benzophenone hydrazone, triphenylmethyl iodide, benzyl halide and the like;

R⁴ is a protecting group for carboxyl or the hydroxyl in phosphoric acid, especially C$_{1-6}$ alkyl optionally substituted with one or more phenyls, such as methyl, ethyl, diphenylmethyl, triphenylmethyl, benzyl and the like;

In addition, as described above, a compound of general formula (I) can also be converted into a compound of general formula (II) or (III) through conventional chemical means. For example, a compound of general formula (I) can be converted into a corresponding carboxylate (II) through a neutralization reaction, or into a corresponding acyl halide or mixed sulfonic anhydride (III) through reacting with a halogenating agent (such as thionyl chloride or phosphorus halide) or sulfonyl chloride.

To investigate whether the configuration of compound changes in the subsequent reaction processes when the α-C of the carboxyl in starting material (IV) is a chiral carbon atom, the inventors design a method as shown in following Reaction Scheme 3.

Reaction Scheme 3

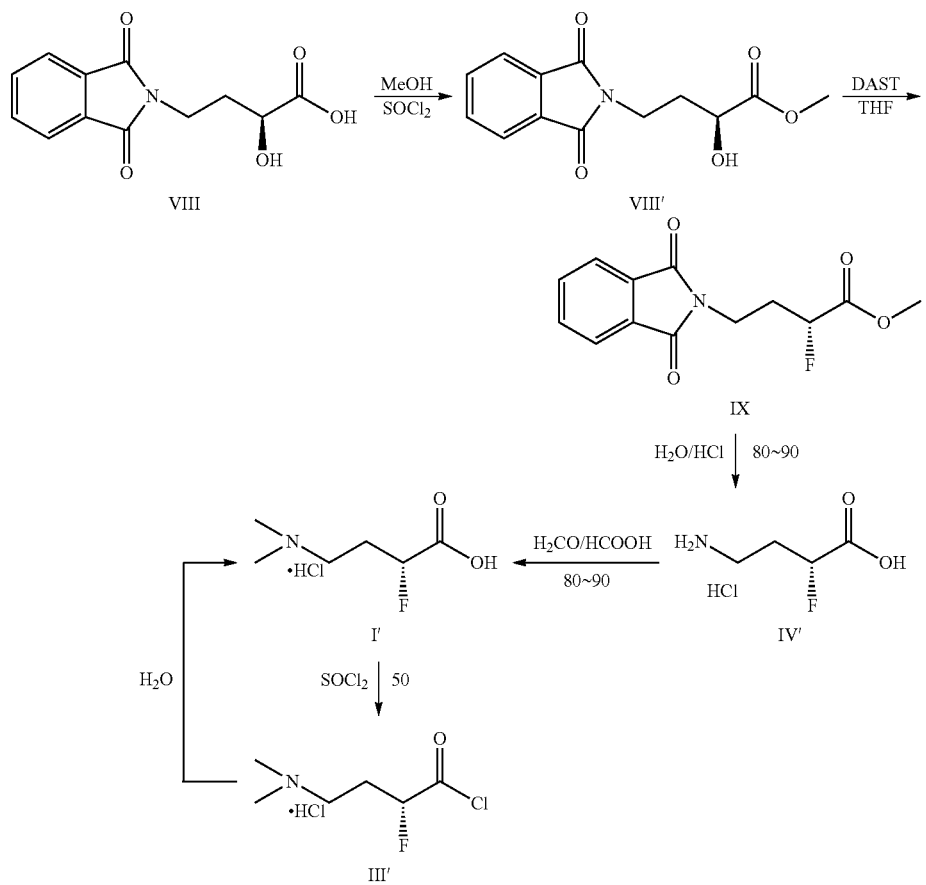

R⁵ is a protecting group for the carboxyl at position 1, such as methyl, alkyl substituted with silyl, 9-fluorenylmethyl, tert-butyl, benzyl and the like.

The compounds of general formulae (IV) and (V) (including the compounds of general formulae (Va), (Vb) and (Vc)) in the above reaction schemes can be obtained by methods reported in relevant references, e.g. [1] Chem. Commun. 1999:1739-1740; [2] J. Med. Chem, 2001, 44:2849-2856; [3] JCS Perkin I 1980:2029-2032; [4] Journal of Fluorine Chemistry (23), 1983:241-259; [5] Journal of Fluorine Chemistry, 2004, 125 (4): 509-515; [6] Phosphorus, Sulfur and Silicon and the Related Elements, 1995, 105 (1-4): 205-212; [7] Tetrahedron Letters, 2007, 48 (4): 711-714; [8] Helvetica Chimica Acta, 1958: 1163-1167; and [9] Justus Liebigs Annalen der Chemie, 1962, 655:70-80.

The compound of formula (VIII) in S configuration ([a]$_D^{24}$=+14.91° (c=0.209 g/100 ml, MeOH), as a starting material, is esterified before replacing the hydroxyl group with fluorine using a fluorinating agent, DAST, so as to obtain the compound of formula (IX) ([a]$_D^{25.7}$=−5.04° (c=0.453 g/100 ml, MeOH)). In above Reaction Scheme 3, the reaction for preparing the compound of formula (IX) by fluorinating the compound of formula (VIII') is an SN$_2$ reaction, wherein the configuration of the chiral carbon atom is inverted [see, e.g., (1). J. ANTIBIOTIC, 1990, 43(7), 858-872; (2). J.O.C, 1979, 44, 3406]. The circular dichroism spectra and the measurement of optical activity of the resulting compound are consistent with those reported in references. The compound of formula (IV') is obtained by the hydrolysis of the compound of formula (IX), and the compound of formula (I') ($[\alpha]_D^{26}=-9.36$ (c=0.315 g/100 ml, H₂O)) and the compound of formula (III') can be prepared by the methods as describe above. The compound of formula (III') can be hydrolyzed to obtain the compound of formula (I'). It is shown by the circular dichroism spectra and the measurement of optical activity that the configuration of the compound of formula (I') is consistent with that of the compound of formula (IX). It can be concluded that when the α-C of carboxyl in the compound of general formula (IV) is a chiral carbon atom, the configuration of compound does not change in the subsequent reaction processes for preparing the compound of general formula (I).

Use for the Preparation of a Prodrug

The carboxylic acid derivative of the present invention can react with a hydroxyl group in a poorly soluble drug to give an ester, so as to obtain a water soluble prodrug.

For example, the carboxylic acid derivative of the present invention can form the following water soluble prodrug (wherein Y=F) with docetaxel:

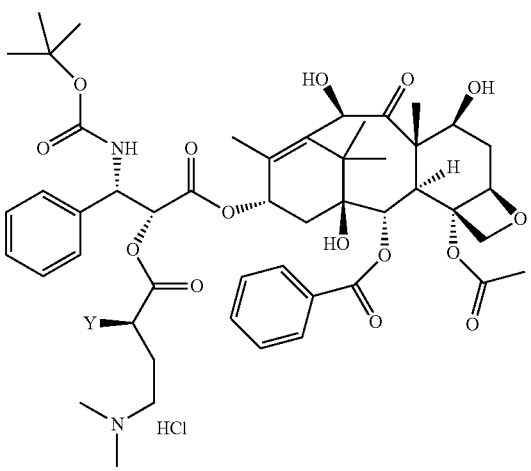

(J)

The inventors also prepared a control compound (J-1) of the above compound (J), which only differed from compound (J) in that Y=H.

The inventors administered solutions of the docetaxel derivative of general formula (J) and the control compound (J-1) in physiological saline to mice via intravenous injection, respectively.

Blood was taken for detection 5-10 minutes after injection of the control compound (J-1) wherein Y=H. The detection result showed that the percentage of the control compound (J-1) was higher than that of docetaxel in blood plasma.

Blood was taken for detection immediately after injection of the docetaxel derivative (J) wherein Y=F. The detection result showed that the docetaxel derivative (J) was almost completely dissociated into docetaxel in blood plasma.

For another example, the carboxylic acid derivative of the present invention can form the following water soluble prodrug (wherein Y=F) with propofol:

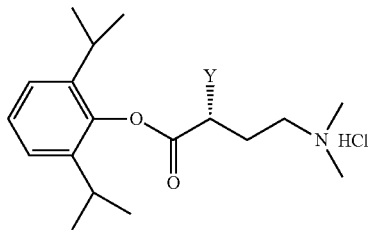

(J')

The inventors also prepared a control compound (J'-1) of above compound (J'), which only differed from compound (J') in that Y=H.

The inventors administered the propofol derivative of general formula (J') and the control compound (J'-1) in equimolar amounts to propofol to mice via intravenous injection, respectively, and observed the following results:

For the control compound (J'-1) wherein Y=H, the latent period and persistent period for anesthesia were much longer than those of propofol, and the mice suffered from transient hemiplegia after waking up.

For the propofol derivative (J') wherein Y=F, the latent period and persistent period for anesthesia were almost equal to those of propofol, and no neurotoxic response was observed.

In addition, the inventors dissolved the compound of the present invention having the following formula in physiological saline, adjusted the pH of the solution to 7.4, and administered the solution to mice through the caudal vein. The LD₅₀ thus detected was higher than 1500 mg/kg.

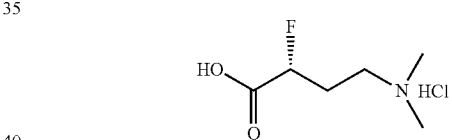

As can be seen from the above, the carboxylic acid derivative of the present invention can react with a hydroxyl group in a poorly soluble drug through chemical processes to increase the water solubility of the poorly soluble drug, so as to obtain a water soluble prodrug suitable for injection. Surprisingly, the prodrug thus obtained can be easily dissociated in vivo to release the parent drug, without affecting the physiological activity of the prodrug. As a result, the side effects caused by a high molecular co-solvent in an injection of the parent drug can be reduced. Thus, the carboxylic acid derivative of the present invention is a suitable ligand for a prodrug.

EXAMPLES

To make the purpose and technical solutions of the present invention more clear, the preferable examples of the present invention are described in detail as follows. It should be noted that the following examples are provided merely for further illustration of the present invention, but should not be construed to limit the scope of the present invention. Any non-essential modifications and/or adjustments to the technical solutions of the present invention by a person skilled in the art based on the above disclosure of the present invention all fall within the protection scope of the present invention.

Example 1

Preparation of 4-N,N-dimethylamino-2(R)-fluorobutyric Acid Hydrochloride 4-amino-2(R)-fluorobutyric acid hydrochloride (1.1 g, 7.0 mmol) was added to a round bottom flask, a saturated aqueous $Na_2CO_3$ solution was added to adjust the pH value to 8, and then 88% formic acid (6 ml) and 35% aqueous formaldehyde solution (5 ml) were added. The reaction mixture was warmed slowly to 80° C., and was allowed to react for 15 hours. The reaction mixture was cooled to room temperature, and 6 N hydrochloric acid (2 ml) was added followed by concentration under reduced pressure to obtain a light yellow solid. The solid was dissolved in methanol (10 ml), and the resulting solution was cooled in an ice bath with stirring for 30 min. Then the resulting mixture was filtered, and the filtrate was concentrated. The residue was refluxed in 6 N hydrochloric acid (100 ml) for 4 hours, and the liquid was removed by rotary evaporation. The solid thus obtained was treated with acetonitrile to obtain a white solid (1.1 g, yield: 85%).

m.p.: 136-138° C.;
$^1$H-NMR (400 MHz, $D_2O$): δ 4.72 (ddd, 1H), 2.90 (dtd, 2H), 2.43 (s, 6H), 1.93 (m, 2H);
$^{13}$C-NMR (600 MHz, $D_2O$): δ 173.13, 86.90, 53.49, 42.83, 26.91;
ESI-MS m/z $[M-C]^+$ 150.13.

Example 2

Preparation of 4-N-isopropylamino-2(R,S)-fluorobutyric Acid Hydrochloride 4-amino-2(R,S)-fluorobutyric acid hydrochloride (1.1 g, 7.0 mmol) was added to a round bottom flask (50 ml), a saturated aqueous $Na_2CO_3$ solution was added to adjust the pH to 8, and then acetone (15 ml) and 5% Pd—C(100 mg) were added. Air was replaced with nitrogen, which was then replaced with hydrogen. The reaction was carried out for 6 hours at room temperature. Pd—C was removed through filtration, and the pH of the solution was adjusted to be acidic with 6 N hydrochloric acid. The solution was concentrated under reduced pressure to obtain a light yellow solid. The solid was dissolved in methanol (10 ml), and the resulting solution was cooled in an ice bath with stirring for 30 min. Then the resulting mixture was filtered, and the filtrate was concentrated. The residue was refluxed in 6 N hydrochloric acid (100 ml) for 4 hours, and the solvent was removed by rotary evaporation. The solid thus obtained was treated with acetonitrile to obtain a white solid (1.05 g, yield: 75%).

ESI-MS m/z $[M-C]^+$ 164.12.

Example 3

Preparation of 4-N,N-diethylamino-2(R,S)-trifluoromethylbutyric Acid Hydrochloride 4-amino-2(R,S)-trifluoromethylbutyric acid hydrochloride (2.07 g, 10 mmol) was added to a round bottom flask (50 ml), and 1 N aqueous $NaHCO_3$ solution was added to adjust the pH value to 8. Acetonitrile (50 ml) was added, and a mixed solution (10 ml) of bromoethane (2.18 g, 20 mmol) and acetonitrile was added dropwise. The pH of the reaction solution was maintained at 7-8 with a solution of sodium bicarbonate. Hydrochloric acid was added to adjust the pH to below 5 after completion of the reaction, and the solution was concentrated under reduced pressure to obtain a light yellow solid. Methanol (10 ml) was added, the resulting solution was stirred for 30 min before filtration, and the filtrate was concentrated. The residue was refluxed in 6 N hydrochloric acid (100 ml) for 4 hours, the solvent was removed by rotary evaporation, and a white solid (yield: 13%) was obtained.

ESI-MS m/z $[M-C]^+$ 228.16.

Example 4

Preparation of 4-N-benzylamino-2,2-difluorobutyric Acid Hydrochloride

The title compound was prepared according to the method of Example 2, using 4-amino-2,2-difluorobutyric acid hydrochloride (1.1 g, 5.6 mmol) and benzaldehyde as starting materials.

ESI-MS m/z $[M-C]^+$ 230.06.

Example 5

Preparation of 4-N-isobutylamino-2(R,S)-difluoromethylbutyric Acid Hydrochloride The title compound was prepared according to the method of Example 2, using 4-amino-2(R,S)-difluoromethylbutyric acid hydrochloride (1.90 g, 10 mmol) and butanone (15 ml) as starting materials, and a white solid (1.1 g, yield: 45%) was obtained.

m.p.: 141-142° C.;
ESI-MS m/z $[M-C]^+$ 210.1.

Example 6

Preparation of 4-N-(aziridin-1-yl)-2(R,S)-difluoromethylbutyric Acid Hydrochloride 4-amino-2(R,S)-difluoromethylbutyric acid hydrochloride (1.90 g, 10 mmol) was added to a round bottom flask (50 ml), an aqueous $NaHCO_3$ solution was added to adjust the pH to 7-8, and acetonitrile (15 ml) and 1-chloro-2-bromoethane (10 mmol) were added. The reaction was carried out at ambient temperature for 0.5 h, and then the reaction mixture was heated to reflux and was allowed to react under reflux for 2 h. The solvent was removed by evaporation under reduced pressure, and methanol (10 ml) was added to the residue. The resulting solution was then cooled in an ice bath with stirring for 30 min before filtration, and the filtrate was concentrated. The residue was refluxed in 6 N hydrochloric acid (100 ml) for 4 hours, the solvent was removed by rotary evaporation, and a white solid (0.7 g) was obtained.

ESI-MS m/z $[M-C]^+$ 180.14.

Example 7

Preparation of 4-N-(pyrrolidin-1-yl)-2(R,S)-fluorobutyric Acid Hydrochloride The title compound was prepared according to the method of Example 6, using 4-amino-2(R,S)-fluorobutyric acid and 1-chloro-4-bromobutane as starting materials.

ESI-MS m/z $[M-C]^+$ 176.1.

Example 8

Preparation of 3-N-benzylamino-2(R,S)-(1,1-difluoromethyl)propionic Acid Hydrochloride The title compound was prepared according to the method of Example 2, using 3-amino-2(R,S)-(1,1-difluoromethyl)propionic acid hydrochloride and benzaldehyde as starting materials.

ESI-MS m/z [M−C]$^+$ 230.19.

Example 9

Preparation of 6-N-cyclohexylamino-2(R,S)-trifluoromethylhexanoic Acid Hydrochloride The title compound was prepared according to the method of Example 2, using 6-amino-2(R,S)-trifluoromethylhexanoic acid hydrochloride and cyclohexanone as starting materials.

ESI-MS m/z [M−C]$^+$ 282.08.

Example 10

Preparation of 4-benzyloxy-4-oxo-2(R,S)-fluorobutyric Acid

At room temperature, 2(R,S)-fluorosuccinic acid (10 mmol) was dissolved in methanol (30 ml), and the resulting solution was stirred for 2 h. The solvent was removed by evaporation under reduced pressure, and 1-methyl 2(R,S)-fluorosuccinate was obtained.

ESI-MS m/z [M−H]$^-$ 149.01.

At room temperature, 1-methyl 2(R,S)-fluorosuccinate (5 mmol) was dissolved in dry dichloromethane (20 ml), and thionyl chloride (0.3 ml) was added. The reaction mixture was heated slowly to reflux, and was allowed to react for 3 h. The remaining thionyl chloride and solvent were removed by evaporation under reduced pressure, and fluorobutyryl chloride was obtained.

Under cooling in an ice bath, a solution of fluorobutyryl chloride (4 mmol) in dichloromethane (5 ml) was added dropwise to a solution of benzyl alcohol (4 mmol) and pyridine (5 mmol) in dichloromethane (10 ml), and the reaction was carried out under ice cooling for 1 h. The organic layer was washed with an aqueous solution of hydrochloric acid (pH 3), and was dried over anhydrous sodium sulfate. The solvent was removed by evaporation under reduced pressure, and methyl 4-benzyloxy-4-oxo-2(R,S)-fluorobutyrate was obtained.

ESI-MS m/z [M+H]$^+$ 241.18.

Under cooling in an ice bath, methyl 4-benzyloxy-4-oxo-2(R,S)-fluorobutyrate (7 mmol) was dissolved in methanol (10 ml), 1 N NaOH solution (1 ml) was added, and the reaction was carried out under ice cooling for 1 h. Methanol was removed by evaporation under reduced pressure, water (10 ml) was added, and the pH of the reaction was neutralized to below 1 with 1 N hydrochloric acid. The aqueous layer was extracted with diethyl ether, and the diethyl ether layers were combined, dried over anhydrous sodium sulfate, and filtered. The solvent was removed by evaporation under reduced pressure, and 4-benzyloxy-4-oxo-2(R,S)-fluorobutyric acid (yield: 40%) was obtained.

ESI-MS m/z [M−H]$^-$ 225.18.

Example 11

Preparation of 5-benzyloxy-5-oxo-2(R)-fluoropentanoic acid

The title compound was prepared according to the method of Example 10, using 2(R)-fluoroglutaric acid as a starting material.

ESI-MS m/z [M−H]$^-$ 239.19.

Example 12

Preparation of 6-benzyloxy-6-oxo-2(S)-fluorohexanoic Acid

The title compound was prepared according to the method of Example 10, using 2(S)-fluoroadipic acid as a starting material.

ESI-MS m/z [M−]$^-$ 253.17

Example 13

Preparation of dibenzyl [1-(3-(R,S)-fluoro-3-carboxy)propyl] phosphate Triester

At room temperature, [1-(3-(R,S)-fluoro-3-carboxy)propyl] phosphate monoester (10 mmol) was dissolved in methanol (10 ml), and the resulting solution was stirred for 1 h. Methanol was removed by evaporation under reduced pressure, and [1-(3-(R,S)-fluoro-4-oxo-4-methoxy)butyl] phosphate monoester was obtained.

ESI-MS m/z [M−]$^-$ 215.07.

At room temperature, [1-(3-(R,S)-fluoro-4-oxo-4-methoxy)butyl] phosphate monoester (7 mmol) was dissolved in dry acetonitrile (20 ml), anhydrous potassium carbonate (17 mmol) and benzyl bromide (17 mmol) were added, and the reaction mixture was heated slowly to reflux. After completion of the reaction as monitored by TLC, the reaction mixture was cooled and filtered, and the solvent was removed by rotary evaporation. The residue was purified by column chromatography (EA:PE=1:3), and dibenzyl [1-(3-(R,S)-fluoro-4-oxo-4-methoxy)butyl] phosphate triester was obtained.

ESI-MS m/z [M+H]$^+$ 397.08.

Under cooling in an ice bath, dibenzyl [1-(3-(R,S)-fluoro-4-oxo-4-methoxy)butyl]phosphate triester (10 mmol) was dissolved in tetrahydrofuran (10 ml), 1 N NaOH solution (1 ml) was added slowly, and the reaction mixture was stirred under ice cooling for 1 h until a white solid precipitated. The reaction mixture was filtered, the filter cake was dissolved in water (10 ml), and the pH was adjusted to below 1 with concentrated hydrochloric acid. The aqueous layer was extracted with diethyl ether, and the diethyl ether layers were combined and dried over anhydrous sodium sulfate. Diethyl ether was removed by rotary evaporation to obtain the product (yield: 63.5%).

ESI-MS m/z [M−]$^-$ 381.29.

Example 14

Preparation of dibenzyl [1-(5-(S)-fluoro-5-carboxy)pentyl] phosphate Triester

The title compound was prepared according to the method of Example 13, using [1-(5-(S)-fluoro-5-carboxy)pentyl] phosphate monoester as a starting material.

ESI-MS m/z [M−]$^-$ 409.29

Example 15

Preparation of 4-(dibenzyloxy)phosphoryl-2(R,S)-fluorobutyric Acid

The title compound was prepared according to the method of Example 13, using 4-(dihydroxy)phosphoryl-2(R,S)-fluorobutyric acid as a starting material.
ESI-MS m/z [M−]⁻ 365.28

Example 16

Preparation of 5-(dibenzyloxy)phosphoryl-2(R)-fluoropentanoic Acid

The title compound was prepared according to the method of Example 13, using 5-(dihydroxy)phosphoryl-2(R)-fluoropentanoic acid as a starting material.
ESI-MS m/z [M−H]⁻ 379.31.

According to the methods of the above examples, the inventors also prepared the following compounds:
4-benzyloxy-4-oxo-2(R,S)-fluorobutyryl chloride (ESI-MS m/z [M+H]⁺245.01);
sodium 5-benzyloxy-5-oxo-2(R)-fluorovalerate (ESI-MS m/z [M−Na]⁻239.07);
dibenzyl [1-(3-(R,S)-fluoro-4-oxo-4-chloro)butyl] phosphate triester (ESI-MS m/z [M+H]⁺401.02);
   dibenzyl [potassium 1-(4-(S)-fluoro-5-carboxylate)pentyl] phosphate triester (ESI-MS m/z [M−K]⁻395.11);
4-(dibenzyloxy)phosphoryl-2(R,S)-fluorobutyryl chloride (ESI-MS m/z [M+H]⁺385.04);
sodium 4-N,N-dimethylamino-2(R,S)-fluorobutyrate (ESI-MS m/z [M−Na] 149.03);
calcium 4-N,N-diethylamino-2(R,S)-fluorobutyrate (ESI-MS m/z [(M−Ca)/2]⁻177.08);
aluminum 3-N-benzylamino-2(R,S)-benzyloxypropionate (ESI-MS m/z [(M−Al)/3]⁻284.13);
4-N,N-dimethylamino-2(R,S)-fluorobutyryl chloride hydrochloride (ESI-MS m/z [M−Cl]⁺168.01);
4-N-benzylamino-2,2-difluorobutyryl chloride hydrochloride (ESI-MS m/z [M−Cl]⁺248.03);
4-N,N-dimethylamino-2(R,S)-fluorobutyric acid (ESI-MS m/z [M+H]⁺150.08); and
4-N,N-dimethylamino-2(S)-fluorobutyric acid hydrochloride (ESI-MS m/z [M−Cl]⁺150.11).

The inventors prepared water soluble prodrugs by reactions between specified compounds of the present invention and taxane drugs, specifically as follows.

Example 17

2'-O-[4-(N,N-dimethyl)amino-2(R)-fluorobutyryl] paclitaxel Hydrochloride (Compound No. 01)

1) Preparation of 4-N,N-dimethylamino-2(R)-fluorobutyryl chloride hydrochloride: 4-(N,N-dimethyl)amino-2(R)-fluorobutyric acid hydrochloride (10 mmol) was placed in thionyl chloride (10 ml). The reaction mixture was slowly warmed to 40° C., and was allowed to react for 4 h. Thionyl chloride was removed by evaporation under reduced pressure, anhydrous dichloromethane (DCM) was added, and the solvent was removed by evaporation under reduced pressure after stirring. Anhydrous dichloromethane (60 ml) was added to the residue to obtain a solution for the next step.

2) At −50° C., paclitaxel (1.6 g) and 4-N,N-dimethylaminopyridine (1.4 g) were added to dichloromethane (DCM, 150 ml), and the resulting mixture was stirred for dissolution. The solution of 4-N,N-dimethylamino-2(R)-fluorobutyryl chloride hydrochloride in dichloromethane obtained in step 1) was slowly added dropwise. The reaction was monitored by HPLC. Upon completion of the reaction, the DCM layer was washed with a saturated aqueous sodium chloride solution (the pH of which was adjusted to about 3.0 with hydrochloric acid), dried over anhydrous sodium sulfate, and filtered. DCM was removed by rotary evaporation to obtain the title compound (yield: 50%).
ESI-MS m/z [M−Cl]⁺:985.4.
¹H-NMR (400 MHz, DMSO):δ 7.86 (m, 2H), 7.79 (m, 2H), 7.68 (t, 1H), 7.59 (m, 3H), 7.48 (t, 2H,), 7.38(m, 2H), 7.25 (m, 3H), 6.18 (s, 1H), 6.15 (s, 1H), 5.79 (s, 1H), 4.98 (t, 2H), 4.85(d, J=6.24 Hz, 1H), 4.26 (d, 1H,), 3.72 (d=7.62 Hz, 1H), 3.64(t, 1H), 2.89 (t, 2H), 2.54 (s, 1H), 2.26 (t, 2H), 2.18 (m, 13H), 2.01 (s,3 H), 1.95 (m, 2H), 1.86 (m, 1H), 1.75 (m, 1H), 1.68 (m, 1H), 1.52 (s, 6H), 1.41 (s, 3H).
¹³C-NMR (600 MHz, DMSO):δ 203.64, 171.32, 169.63, 168.96, 165.98, 165.86, 140.36, 140.21, 137.12, 134.65, 134.12, 133.98, 133.89, 133.21, 130.65, 129.94, 128.98, 128.54, 128.43, 128.12, 85.12, 81.45, 80.65, 78.23, 76.58, 76.46, 76.45, 74.98, 72.56, 70.23, 59.64, 54.87, 53.03, 48.65, 43.45, 42.26, 42.15, 41.96, 38.96, 34.45, 28.20, 23.97, 21.65, 21.01, 11.23.

Example 18

2'-O-[4-(N,N-dimethyl)amino-2(R,S)-fluorobutyryl] paclitaxel Hydrochloride (Compound No. 03)

At −50° C., paclitaxel (2 g) and 4-N,N-dimethylaminopyridine (1.9 g) were added to dichloromethane (DCM, 150 ml), and the resulting mixture was stirred for dissolution. A solution of 4-N,N-dimethylamino-2(R,S)-fluorobutyryl chloride hydrochloride (prepared according to the method of Example 17, using 4-N,N-dimethylamino-2(R,S)-fluorobutyric acid hydrochloride as a starting material) in dichloromethane was slowly added dropwise Upon completion of the reaction as monitored by HPLC, the DCM layer was washed with a saturated aqueous sodium chloride solution (the pH of which was adjusted to about 3.0 with hydrochloric acid), dried over anhydrous sodium sulfate, and filtered. DCM was removed by rotary evaporation to give a solid (yield: 43%).

Example 19

2'-O-[4-(N,N-dimethyl)amino-2(R)-fluorobutyryl] docetaxel Hydrochloride (Compound No. 04)

At −15° C., docetaxel (2.1 g) and 4-N,N-dimethylaminopyridine (1.8 g) were added to dichloromethane (DCM, 150 ml), and the resulting mixture was stirred for dissolution. A solution of 4-N,N-dimethylamino-2(R)-fluorobutyryl chloride hydrochloride (prepared according to the method of Example 17) in dichloromethane was slowly added dropwise. Upon completion of the reaction as monitored by HPLC, the DCM layer was washed with a saturated aqueous sodium chloride solution (the pH of which was adjusted to about 3.0 with hydrochloric acid), dried over anhydrous sodium sulfate, and filtered. DCM was removed by rotary evaporation to give a solid (yield: 51%).
ESI-MS m/z [M−Cl]⁺:939.54.

¹H-NMR (600 MHz, DMSO): δ 8.00 (d, J=8.0 Hz, 2H, Bz), 7.91 (d, J=9.2 Hz, 1H, —NH), 7.72 (t, J=7.2 Hz, 1H, Bz), 7.65 (t, J=7.8 Hz, 2H, Bz), 7.46-7.39 (m, 4H, Ph), 7.21 (t, J=7.2 Hz, 1H, Ph), 5.84 (t, J=6.6 Hz, 1H), 5.51 (s, 1H), 5.41 (t, J=9.0 Hz, 1H), 5.26 (d, J=6.4 Hz, 1H), 5.17 (t, J=7.8 Hz, 1H), 5.11 (s, 1H, —OH), 5.03 (d, J=7.2 Hz, 1H, —OH), 4.92 (t, J=9.6 Hz, 2H), 4.47 (s, 1H, —OH), 4.05 (t, J=8.4 Hz, 3H), 3.65 (d, J=5.6 Hz, 1H, FCH), 3.13-3.08 (m, 2H), 2.74 (s, 6H, $H_3C$—N—$CH_3$), 2.31 (s, 3H, —Ac), 1.90-1.88 (m, 1H), 1.75 (s, 3H, —$CH_3$), 1.66 (t, J=10.2 Hz, 2H), 1.52 (s, 3H, —$CH_3$), 1.36 (s, 9H, t-Bu), 1.22 (d, J=11.2 Hz, 2H), 1.11 (s, 1H), 1.00 (s, 6H, —$CH_3$).

¹³C-NMR (600 MHz, DMSO): δ 209.458, 169.376, 168.425, 167.682, 167.513, 166.869, 165.229, 155.167, 137.026, 136.896, 135.884, 133.171, 131.278, 129.960, 129.539, 128.542, 128.044, 127.201, 86.406, 85.187, 83.701, 80.367, 79.033, 78.811, 78.596, 76.788, 75.416, 74.703, 73.715, 71.883, 70.710, 67.308, 57.007, 54.708, 51.949, 45.925, 42.867, 42.515, 42.086, 38.077, 36.391, 34.675, 29.777, 28.980, 28.337, 28.061, 26.566, 26.436, 26.298, 23.209, 22.405, 20.627, 13.806, 13.614, 10.717, 9.667.

The following compounds were prepared according to the method of Example 18 or Example 19:

2'-O-[4-(N,N-dimethyl)amino-2(S)-fluorobutyryl]paclitaxel hydrochloride (Compound No. 02);

2'-O-[4-(N,N-dimethyl)amino-2(S)-fluorobutyryl]docetaxel hydrochloride (Compound No. 05);

2'-O-[4-(N,N-dimethyl)amino-2(R,S)-fluorobutyryl]docetaxel hydrochloride (Compound No. 06);

2'-O-[4-(N,N-dimethyl)amino-2(R)-fluorobutyryl]cabazitaxel hydrochloride (Compound No. 07);

2'-O-[4-(N,N-dimethyl)amino-2(S)-fluorobutyryl]cabazitaxel hydrochloride (Compound No. 08);

2'-O-[4-(N,N-dimethyl)amino-2(R,S)-fluorobutyryl]cabazitaxel hydrochloride (Compound No. 09);

2'-O-[4-amino-2(R)-difluoromethylbutyryl]cabazitaxel sodium bisulfate salt (Compound No. 10);

2'-O-[4-(N,N-diethyl)amino-2-methyl-2(R)-2-trifluoromethylbutyryl]cabazitaxel methanesulfonate (Compound No. 11);

2'-O-[5-(N-methyl-N-ethyl)amino-2(R)-2-difluoroethylvaleryl]docetaxel hydrochloride (Compound No. 12);

2'-O-[5-(N,N-dimethyl)amino-2(R)-fluorovaleryl]docetaxel methanesulfonate (Compound No. 13);

2'-O-[7-N-(aziridin-1-yl)-2,2-difluoroheptanoyl]docetaxel methanesulfonate (Compound No. 14);

2'-O-[8-(N-methyl-N-cyclopentyl)amino-2(R,S)-2-trifluoromethyl-2-fluorooctanoyl]paclitaxel methanesulfonate (Compound No. 15);

2'-O-[4-(N,N-dimethyl)amino-2(R)-fluorobutyryl]paclitaxel methanesulfonate (Compound No. C1);

2'-O-[4-(N,N-dimethyl)amino-2(S)-fluorobutyryl]paclitaxel methanesulfonate (Compound No. C2);

2'-O-[4-(N,N-dimethyl)amino-2(R,S)-fluorobutyryl]paclitaxel methanesulfonate (Compound No. C3);

2'-O-[4-(N,N-dimethyl)amino-2(R)-fluorobutyryl]docetaxel methanesulfonate (Compound No. C4);

2'-O-[4-(N,N-dimethyl)amino-2(S)-fluorobutyryl]docetaxel methanesulfonate (Compound No. C5);

2'-O-[4-(N,N-dimethyl)amino-2(R,S)-fluorobutyryl]docetaxel methanesulfonate (Compound No. C6);

2'-O-[4-(N,N-dimethyl)amino-2(R)-fluorobutyryl]cabazitaxel methanesulfonate (Compound No. C7);

2'-O-[4-(N,N-dimethyl)amino-2(S)-fluorobutyryl]cabazitaxel methanesulfonate (Compound No. C8);

2'-O-[4-(N,N-dimethyl)amino-2(R,S)-fluorobutyryl] cabazitaxel methanesulfonate (Compound No. C9);

2'-O-[4-(N-methyl-N-ethyl)amino-2(R)-fluorobutyryl]paclitaxel methanesulfonate (Compound No. 16);

2'-O-[4-(N,N-diethyl)amino-2(S)-fluorobutyryl]paclitaxel fumarate (Compound No. 17);

2'-O-[4-(N-methyl-N-isopropyl)amino-2(R,S)-fluorobutyryl]paclitaxel hydrochloride (Compound No. 18);

2'-O-[4-(N,N-dimethyl)amino-2(R,S)-2-trifluoromethylbutyryl]paclitaxel p-toluene sulfonate (Compound No. 19);

2'-O-[4-(N,N-dimethyl)amino-2(R,S)-2-difluoromethylbutyryl]paclitaxel hydrochloride (Compound No. 20);

2'-O-[5-(N,N-dimethyl)amino-2(R)-fluorovaleryl]paclitaxel maleate (Compound No. 21);

2'-O-[6-(N,N-dimethyl)amino-2(S)-2-difluoromethylhexanoyl]paclitaxel sulfate (Compound No. 22);

2'-O-[4-(N-methyl-N-ethyl)amino-2(R)-fluorobutyryl]docetaxel methanesulfonate (Compound No. 23);

2'-O-[4-(N,N-diethyl)amino-2(S)-fluorobutyryl]docetaxel maleate (Compound No. 24);

2'-O-[4-(N-methyl-N-isopropyl)amino-2(R)-fluorobutyryl] docetaxel hydrochloride (Compound No. 25);

2'-O-[4-(N,N-dimethyl)amino-2(R)-2-trifluoromethylbutyryl] docetaxel methanesulfonate (Compound No. 26);

2'-O-[4-(N,N-dimethyl)amino-2(R,S)-2-difluoromethylbutyryl]docetaxel hydrochloride (Compound No. 27);

2'-O-[5-(N,N-dimethyl)amino-2(R,S)-fluorovaleryl]docetaxel methanesulfonate (Compound No. 28);

2'-O-[6-(N,N-dimethyl)amino-2(S)-fluorohexanoyl]docetaxel sulfate (Compound No. 29);

2'-O-[4-(N-methyl-N-ethyl)amino-2(R)-fluorobutyryl]cabazitaxel maleate (Compound No. 30);

2'-O-[4-(N,N-diethyl)amino-2(R)-fluorobutyryl]cabazitaxel methanesulfonate (Compound No. 31);

2'-O-[4-(N-methyl-N-isopropyl)amino-2(R)-fluorobutyryl] cabazitaxel hydrochloride (Compound No. 32);

2'-O-[4-(N,N-dimethyl)amino-2(R)-2-trifluoromethylbutyryl]cabazitaxel methanesulfonate (Compound No. 33);

2'-O-[4-(N,N-dimethyl)amino-2(R)-2-difluoromethylbutyryl] cabazitaxel p-toluene sulfonate (Compound No. 34);

2'-O-[5-(N,N-dimethyl)amino-2(R)-fluorovaleryl]cabazitaxel hydrochloride (Compound No. 35);

2'-O-[6-(N,N-dimethyl)amino-2(R)-fluorohexanoyl]cabazitaxel sulfate (Compound No. 36);

2'-O-[4-(N,N-diethyl)amino-2(R,S)-fluorobutyryl]cabazitaxel hydrochloride (Compound No. 37);

2'-O-[4-amino-2(R,S)-trifluoromethylbutyryl]docetaxel methanesulfonate (Compound No. 38);

2'-O-[4-(N,N-dimethyl)amino-2(R,S)-difluoromethylbutyryl]paclitaxel citrate (Compound No. 39);

2'-O-[4-(N,N-dimethyl)amino-2(R,S)-fluorobutyryl]docetaxel hydrochloride (Compound No. 40);

2'-O-[4-(N,N-diethyl)amino-2(R)-fluorobutyryl]paclitaxel hydrochloride (Compound No. 41);

2'-O-[4-(N-benzyl)amino-2(S)-fluorobutyryl]docetaxel hydrochloride (Compound No. 42);

2'-O-[4-(N-isopropyl)amino-2(R,S)-trifluoromethylbutyryl] paclitaxel hydrochloride (Compound No. 43);

2'-O-[4-cyclopropylamino-2(R,S)-trifluoromethylbutyryl] cabazitaxel methanesulfonate (Compound No. 44);

2'-O-[4-(N-methyl)amino-2(R)-trifluoromethylbutyryl]paclitaxel hydrochloride (Compound No. 45);

2'-O-[4-(N,N-dimethyl)amino-2(S)-trifluoromethylbutyryl] cabazitaxel hydrochloride (Compound No. 46);

2'-O-[4-(N,N-dimethyl)amino-2(R)-difluoromethylbutyryl] docetaxel hydrochloride (Compound No. 47);

2'-O-[3-(N,N-dimethyl)amino-2(R,S)-fluoropropionyl]paclitaxel hydrochloride (Compound No. 48);

2'-O-[3-(N,N-diethyl)amino-2(R,S)-trifluoromethylpropionyl]docetaxel hydrochloride (Compound No. 49);

2'-O-[3-(N-isopropyl)amino-2(R,S)-difluoromethylpropionyl]cabazitaxel hydrochloride (Compound No. 50);

2'-O-[δ-(N,N-dimethyl)amino-2(R)-fluorovaleryl]paclitaxel hydrochloride (Compound No. 51);

2'-O-[δ-(N,N-dimethyl)amino-2(S)-trifluoromethylvaleryl]docetaxel hydrochloride (Compound No. 52);

2'-O-[4-(N-benzyl)amino-2-methyl-2(R,S)-fluorobutyryl]paclitaxel hydrochloride (Compound No. 53);

2'-O-[3-cyclopentylamino-2-ethyl-2(R,S)-trifluoromethylpropionyl]docetaxel hydrochloride (Compound No. 54);

2'-O-[δ-(N-benzyl)amino-2-benzyl-2(R)-difluoromethylvaleryl]cabazitaxel hydrochloride (Compound No. 55); and 2'-O-[4-(4-piperidin-1-yl)-2(S)-trifluoromethylbutyryl]cabazitaxel hydrochloride (Compound No. 56).

The inventors tested the above taxane derivatives, and found that the taxane derivatives prepared in the present invention had good water solubility, and could be dissociated quickly in blood plasma to release parent drugs, so as to exert antitumor activity. Thus, these taxane derivatives are suitable as prodrugs for taxane drugs.

Moreover, the inventors also prepared water soluble prodrugs by reactions between specified compounds of the present invention and propofol drugs, specifically as follows.

Example 20

Propofol 4-(N,N-dimethyl)amino-2(R,S)-fluorobutyrate Hydrochloride (Compound No. E1)

4-N,N-dimethylamino-2(R. S)-fluorobutyric acid hydrochloride (prepared according to the method of Example 1, using 4-amino-2(R,S)-fluorobutyric acid hydrochloride as a starting material) (10 mmol) was dissolved in thionyl chloride (10 ml). The reaction mixture was warmed slowly to 40° C., and was allowed to react for 4 h. Thionyl chloride was removed by evaporation under reduced pressure, anhydrous dichloromethane (DCM, 15 ml) was added, and the solvent was removed by evaporation under reduced pressure after stirring. Anhydrous dichloromethane (60 ml) was added to the residue, and propofol (4.5 mmol) was added dropwise at −78° C. Then, a solution of 4-N,N-dimethylaminopyridine (8.2 mmol) in dichloromethane (20 ml) was slowly added. The reaction was monitored by HPLC. Upon the reaction was complete, the DCM layer was washed with aqueous hydrochloric acid solution (the pH of which is about 1.0), dried over anhydrous sodium sulfate, and filtered. Most DCM was removed by rotary evaporation, and diethyl ether was slowly added until a large amount of solid precipitated out. The resulting mixture was frozen for crystallization, filtered and dried to give a white solid (yield: 83%).

Example 21

Propofol 4-(N,N-dimethyl)amino-2(R)-fluorobutyrate Hydrochloride (Compound No. E2)

At −30° C., the title compound was prepared according to the method of Example 20, using 4-N,N-dimethylamino-2 (R)-fluorobutyryl chloride hydrochloride (10 mmol), propofol (10 mmol) and DMAP (15 mmol) as starting materials (yield: 87%, purity: 99.4%).

$^1$H-NMR (CDCl$_3$): δ 1.22 (9H, d, Me), 2.10 (3H, m, Me), 2.88 (6H, m, NMe), 3.32 (2H, m, CH$_2$), 5.43 (1H, m, F—CH), 7.21 (3H, m, Ph);

ESI-MS m/z [M−Cl]$^+$ 310.1.

Example 22

Propofol 3-(N,N-diethyl)amino-2(R,S)-fluoropropionate Hydrochloride (Compound No. E18)

Propofol 3-(N,N-diethyl)amino-2(R,S)-fluoropropionate hydrochloride was prepared according to the method of Example 20 at −50° C., using 3-(N,N-diethyl)amino-2(R,S)-fluoropropionyl chloride hydrochloride (7 mmol), propofol (4.4 mmol) and DMAP (10 mmol) as starting materials (yield: 81%). ESI-MS m/z [M−Cl]$^+$ 324.17

Example 23

Propofol 3-N-isopropylamino-2(R,S)-fluoropropionate Hydrochloride (Compound No. E19)

Preparation of propofol 3-N-Cbz-N-isopropylamino-2(R,S)-fluoropropionate: propofol (2.8 mmol) was dissolved in pyridine (1.5 ml), a solution (10 ml) of 3-N-Cbz-N-isopropylamino-2(R,S)-fluoropropionyl chloride (5 mmol) in dichloromethane was added dropwise under cooling in an ice bath. After addition, the reaction mixture was allowed to react at room temperature for more than 1 h with stirring. After completion of the reaction, a HCl solution was added until the pH reaches about 3. The reaction solution was washed with water to neutral. The organic layer was dried over anhydrous sodium sulfate, and filtered, and the solvent was removed by evaporation under reduced pressure. The residue was purified by column chromatography (silica gel: 200-300 mesh), and the solvent was removed by evaporation under reduced pressure to give an oil (0.86 g, yield: 69%).

Preparation of propofol 3-N-isopropylamino-2(R,S)-fluoropropionate hydrochloride: propofol 3-N-Cbz-N-isopropylamino-2(R,S)-fluoropropionate (2g, 4.5 mmol) were dissolved in acetic acid (10 ml), 10% Pd—C(0.5 g) was added, and hydrogen was introduced at room temperature for 3 h. After completion of the reaction, water (5 ml) was added, and the mixture was filtered. Solid NaHCO$_3$ was added to the filtrate under cooling in an ice bath until no bubble was produced. The mixture was extracted with diethyl ether (15 ml×3), and the diethyl ether layer was dried over anhydrous sodium sulfate, and filtered. The diethyl ether layer was concentrated to 6 ml. With stirring under cooling in an ice bath, a saturated diethyl ether solution of HCl was added dropwise until a white solid precipitated out. The resulting mixture was filtered, dried under reduced pressure at room temperature, and a white solid (0.81 g, yield: 52%) was obtained.

ESI-MS m/z [M−Cl]$^+$ 310.3.

The following compounds were prepared according to the methods of Examples 20-23:

propofol 4-(N,N-dimethyl)amino-2(R)-2-trifluoromethylbutyrate hydrochloride (Compound No. E3);

propofol 4-(N-methyl-N-ethyl)amino-2(R,S)-2-fluorobutyrate hydrochloride (Compound No. E4);

propofol 5-(N-methyl-N-benzyl)amino-2(S)-2-fluorovalerate hydrochloride (Compound No. E5);
propofol 3-(N-isopropyl)amino-2(R,S)-2-monofluoromethylpropionate methanesulfonate (Compound No. E6);
propofol 4-N-(aziridin-1-yl)-2(S)-2-fluorobutyrate hydrochloride (Compound No. E7);
propofol 4-(pyrrolidin-1-yl)-2(R)-2-fluorobutyrate hydrochloride (Compound No. E8);
propofol 4-carboxyl-2(R,S)-fluorovalerate sodium salt (Compound No. F1);
propofol 4-carboxyl-2(S)-fluorovalerate potassium salt (Compound No. F2);
propofol 4-carboxyl-2(R)-2-trifluoromethyl valerate lithium salt (Compound No. F3);
di[propofol 7-carboxyl-2(R,S)-fluorocaprylate] calcium salt (Compound No. F4);
di[propofol 5-carboxyl-2(S)-fluorohexanoate] zinc salt (Compound No. F5);
tri[propofol 8-carboxyl-2(R,S)-monofluoromethylpelargonate] aluminum salt (Compound No. F6);
propofol 3-carboxyl-2(R)-fluorobutyrate sodium salt (Compound No. F7);
propofol 2-carboxyl-2(S)-fluoropropionate sodium salt (Compound No. F8);
{1-[4-(2,6-diisopropylphenoxy)-4-oxo-3-(R,S)-3-fluoro-1-butyl]} phosphate monoester dipotassium salt (Compound No. G1);
{1-[4-(2,6-diisopropylphenoxy)-4-oxo-3-(S)-3-fluoro-1-butyl]} phosphate monoester disodium salt (Compound No. G2);
{1-[4-(2,6-diisopropylphenoxy)-4-oxo-3-(R)-3-trifluoromethyl-1-butyl]} phosphate monoester dilithium salt (Compound No. G3);
propofol 4-phosphoryl-2(R,S)-fluorobutyrate calcium salt (Compound No. G4);
propofol 5-phosphoryl-2(S)-fluorovalerate zinc salt (Compound No. G5);
tri[propofol 3-phosphoryl-2(R,S)-2-monofluoromethylpropionate] dialuminum salt (Compound No. G6);
propofol 4-(N-methyl-N-isopropyl)amino-2(R,S)-fluorobutyrate methanesulfonate (Compound No. E9);
propofol 4-(N-methyl-N-benzyl)amino-2(R,S)-trifluoromethylbutyrate hydrochloride (Compound No. E10);
propofol 4-(N-cyclopropyl-N-methyl)amino-2(R)-difluoromethylbutyrate hydrochloride (Compound No. E11);
propofol 3-(pyrrolidin-1-yl)-2(S)-trifluoromethylpropionate hydrochloride (Compound No. E12);
propofol 5-N-cyclopentylamino-2,2-difluorovalerate hydrochloride (Compound No. E13);
propofol 6-(N,N-dimethyl)amino-2(R)-fluorovalerate hydrochloride (Compound No. E14);
propofol 3-N-methyl-N-cyclohexylamino-2(R,S)-fluoropropionate hydrochloride (Compound No. E15);
propofol 4-(N,N-dimethyl)amino-2(R)-trifluoromethylbutyrate hydrochloride (Compound No. E16);
propofol 4-N-methyl-N-benzylamino-2(R)-fluorobutyrate hydrochloride (Compound No. E17);
propofol-2(R)-fluoropropionate monoester sodium salt (Compound No. F9);
propofol 4-carboxyl-2(R)-fluorobutyrate sodium salt (Compound No. F10);
propofol 4-carboxyl-2(S)-trifluoromethylbutyrate ammonium salt (Compound No. F11);
propofol 5-carboxyl-2(R,S)-difluoromethylvalerate potassium salt (Compound No. F12);
{1-[3-(2,6-diisopropylphenoxy)-3-oxo-2(R)-fluoro-1-propyl]} phosphate monoester dipotassium salt (Compound No. G7);
{1-[4-(2,6-diisopropylphenoxy)-4-oxo-2(R)-trifluoromethyl-1-butyl]} phosphate monoester dilithium salt (Compound No. G8);
{1-[6-(2,6-diisopropylphenoxy)-6-oxo-5-(S)-difluoromethyl-1-hexyl]} phosphate diarginine salt (Compound No. G9);
propofol 4-phosphoryl-2(R)-fluorobutyrate disodium salt (Compound No. G10);
propofol 3-phosphoryl-2(R,S)-fluoropropionate zinc salt (Compound No. G11).

The inventors tested the above propofol derivatives, and found that the propofol derivatives prepared in the present invention had good water solubility, and could be dissociated quickly in blood plasma to release parent drugs, so as to exert activity. Thus, these propofol derivatives are suitable as prodrugs for propofol drugs.

To further illustrate the use of the carboxylic acid derivative of the present invention for the preparation of a water soluble prodrug, the inventors provide the following experimental examples to show the surprising and unexpected beneficial effects of the carboxylic acid derivative of the present invention as a ligand for a water soluble prodrug, and of the water soluble prodrugs thus prepared.

Experimental Example 1

Examples of the carboxylic acid derivative of the present invention for the preparation of a water soluble taxane prodrug:

When the carboxylic acid mentioned in the present invention is an amino acid, the carboxylic acid derivative can be used for the preparation of a water soluble paclitaxel derivative, a water soluble docetaxel derivative, and a water soluble cabazitaxel derivative. The serial numbers and characterization data of these water soluble taxane prodrugs are as shown in following Table 1:

TABLE 1

The serial numbers and characterization data of the water soluble taxane prodrugs prepared from the carboxylic acid derivatives of the present invention

| Compd. No. | Compd. Name | ESI-MS m/z [M + H]$^+$ |
|---|---|---|
| 01 | 2'-O-[4-(N,N-dimethyl)amino-2(R)-fluorobutyryl]paclitaxel hydrochloride | 985.41 |
| 02 | 2'-O-[4-(N,N-dimethyl)amino-2(S)-fluorobutyryl]paclitaxel hydrochloride | 985.39 |
| 03 | 2'-O-[4-(N,N-dimethyl)amino-2(R,S)-fluorobutyryl]paclitaxel hydrochloride | 985.41 |

TABLE 1-continued

The serial numbers and characterization data of the water soluble taxane prodrugs prepared from the carboxylic acid derivatives of the present invention

| Compd. No. | Compd. Name | ESI-MS m/z [M + H]+ |
|---|---|---|
| 04 | 2'-O-[4-(N,N-dimethyl)amino-2(R)-fluorobutyryl]docetaxel hydrochloride | 939.54 |
| 05 | 2'-O-[4-(N,N-dimethyl)amino-2(S)-fluorobutyryl]docetaxel hydrochloride | 939.55 |
| 06 | 2'-O-[4-(N,N-dimethyl)amino-2(R,S)-fluorobutyryl]docetaxel hydrochloride | 939.57 |
| 07 | 2'-O-[4-(N,N-dimethyl)amino-2(R)-fluorobutyryl]cabazitaxel hydrochloride | 967.59 |
| 08 | 2'-O-[4-(N,N-dimethyl)amino-2(S)-fluorobutyryl]cabazitaxel hydrochloride | 967.62 |
| 09 | 2'-O-[4-(N,N-dimethyl)amino-2(R,S)-fluorobutyryl]cabazitaxel hydrochloride | 967.60 |
| 10 | 2'-O-[4-amino-2(R)-difluoromethylbutyryl]cabazitaxel sodium bisulfate salt | 971.41 |
| 11 | 2'-O-[4-(N,N-diethyl)amino-2-methyl-2(R)-2-trifluoromethylbutyryl]cabazitaxel methanesulfonate | 1059.49 |
| 12 | 2'-O-[4-(N-methyl-N-ethyl)amino-2(R)-2-difluoroethylvaleryl]docetaxel hydrochloride | 1013.45 |
| 13 | 2'-O-[5-(N,N-dimethyl)amino-2(R)-fluorovaleryl]docetaxel methanesulfonate | 953.43 |
| 14 | 2'-O-[5-N-(aziridin-1-yl)-2,2-difluoroheptanoyl]docetaxel methanesulfonate | 997.53 |
| 15 | 2'-O-[7-(N-methyl-N-cyclopentyl)amino-2(R,S)-2-trifluoromethyl-2-fluorooctanoyl]paclitaxel methanesulfonate | 1163.46 |
| C1 | 2'-O-[8-(N,N-dimethyl)amino-2(R)-fluorobutyryl]paclitaxel methanesulfonate | 985.38 |
| C2 | 2'-O-[4-(N,N-dimethyl)amino-2(S)-fluorobutyryl]paclitaxel methanesulfonate | 985.37 |
| C3 | 2'-O-[4-(N,N-dimethyl)amino-2(R,S)-fluorobutyryl]paclitaxel methanesulfonate | 985.41 |
| C4 | 2'-O-[4-(N,N-dimethyl)amino-2(R)-fluorobutyryl]docetaxel methanesulfonate | 939.52 |
| C5 | 2'-O-[4-(N,N-dimethyl)amino-2(S)-fluorobutyryl]docetaxel methanesulfonate | 939.55 |
| C6 | 2'-O-[4-(N,N-dimethyl)amino-2(R,S)-fluorobutyryl]docetaxel methanesulfonate | 939.56 |
| C7 | 2'-O-[4-(N,N-dimethyl)amino-2(R)-fluorobutyryl]cabazitaxel methanesulfonate | 967.58 |
| C8 | 2'-O-[4-(N,N-dimethyl)amino-2(S)-fluorobutyryl]cabazitaxel methanesulfonate | 967.54 |
| C9 | 2'-O-[4-(N,N-dimethyl)amino-2(R,S)-fluorobutyryl]cabazitaxel methanesulfonate | 967.62 |
| 16 | 2'-O-[4-(N-methyl-N-ethyl)amino-2(R)-fluorobutyryl]paclitaxel methanesulfonate | 999.4 |
| 17 | 2'-O-[4-(N,N-diethyl)amino-2(S)-fluorobutyryl]paclitaxel fumarate | 1013.4 |
| 18 | 2'-O-[4-(N-methyl-N-isopropyl)amino-2(R,S)-fluorobutyryl]paclitaxel hydrochloride | 1013.4 |
| 19 | 2'-O-[4-(N,N-dimethyl)amino-2(R,S)-2-trifluoromethylbutyryl]paclitaxel p-toluene sulfonate | 1035.4 |
| 20 | 2'-O-[4-(N,N-dimethyl)amino-2(R,S)-2-difluoromethylbutyryl]paclitaxel hydrochloride | 1017.4 |
| 21 | 2'-O-[5-(N,N-dimethyl)amino-2(R)-fluorovaleryl]paclitaxel maleate | 999.3 |
| 22 | 2'-O-[6-(N,N-dimethyl)amino-2(S)-2-difluoromethylhexanoyl]paclitaxel sulfate | 1045.4 |
| 23 | 2'-O-[4-(N-methyl-N-ethyl)amino-2(R)-fluorobutyryl]docetaxel methanesulfonate | 953.44 |
| 24 | 2'-O-[4-(N,N-diethyl)amino-2(S)-fluorobutyryl]docetaxel maleate | 967.45 |
| 25 | 2'-O-[4-(N-methyl-N-isopropyl)amino-2(R)-fluorobutyryl]docetaxel hydrochloride | 967.42 |
| 26 | 2'-O-[4-(N,N-dimethyl)amino-2(R)-2-trifluoromethylbutyryl]docetaxel methanesulfonate | 989.38 |
| 27 | 2'-O-[4-(N,N-dimethyl)amino-2(R,S)-2-difluoromethylbutyryl]docetaxel hydrochloride | 971.35 |
| 28 | 2'-O-[5-(N,N-dimethyl)amino-2(R,S)-fluorovaleryl]docetaxel methanesulfonate | 953.47 |
| 29 | 2'-O-[6-(N,N-dimethyl)amino-2(S)-fluorohexanoyl]docetaxel sulfate | 967.41 |
| 30 | 2'-O-[4-(N-methyl-N-ethyl)amino-2(R)-fluorobutyryl]cabazitaxel maleate | 981.35 |
| 31 | 2'-O-[4-(N,N-diethyl)amino-2(R)-fluorobutyryl]cabazitaxel methanesulfonate | 995.51 |
| 32 | 2'-O-[4-(N-methyl-N-isopropyl)amino-2(R)-fluorobutyryl]cabazitaxel hydrochloride | 995.47 |

TABLE 1-continued

The serial numbers and characterization data of the water soluble taxane prodrugs prepared from the carboxylic acid derivatives of the present invention

| Compd. No. | Compd. Name | ESI-MS m/z [M + H]+ |
|---|---|---|
| 33 | 2'-O-[4-(N,N-dimethyl)amino-2(R)-2-trifluoromethylbutyryl]cabazitaxel methanesulfonate | 1017.52 |
| 34 | 2'-O-[4-(N,N-dimethyl)amino-2(R)-2-difluoromethylbutyryl]cabazitaxel p-toluene sulfonate | 999.46 |
| 35 | 2'-O-[5-(N,N-dimethyl)amino-2(R)-fluorovaleryl]cabazitaxel hydrochloride | 981.33 |
| 36 | 2'-O-[6-(N,N-dimethyl)amino-2(R)-fluorohexanoyl]cabazitaxel sulfate | 995.34 |

Experimental Example 1.1. Solubility in Physiological Saline

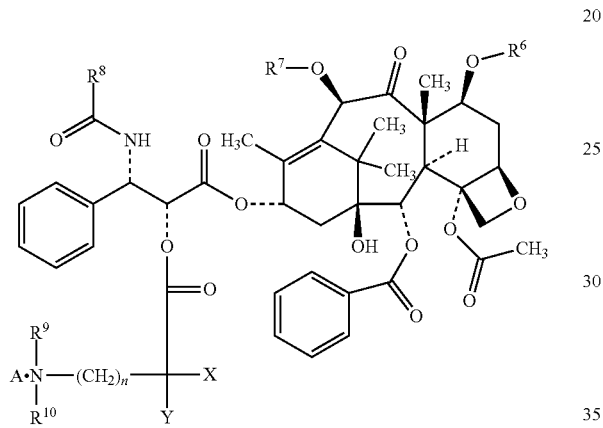

TABLE 2

Solubility of the water soluble taxane derivatives in physiological saline

| Compd. No. | n | $R^6$ | $R^7$ | $R^8$ | $R^9$ | $R^{10}$ | X | Y | C* | A | Solubility (mg/ml) |
|---|---|---|---|---|---|---|---|---|---|---|---|
| 01 | 2 | H | Ac | Ph | Me | Me | H | F | R | HCl | 1.1 |
| 02 | 2 | H | Ac | Ph | Me | Me | H | F | S | HCl | 1.7 |
| 03 | 2 | H | Ac | Ph | Me | Me | H | F | R,S | HCl | 1.1 |
| 04 | 2 | H | H | t-BuO | Me | Me | H | F | R | HCl | 2.8 |
| 05 | 2 | H | H | t-BuO | Me | Me | H | F | S | HCl | 2.5 |
| 06 | 2 | H | H | t-BuO | Me | Me | H | F | R,S | HCl | 2.6 |
| 07 | 2 | Me | Me | t-BuO | Me | Me | H | F | R | HCl | 1.5 |
| 08 | 2 | Me | Me | t-BuO | Me | Me | H | F | S | HCl | 1.3 |
| 09 | 2 | Me | Me | t-BuO | Me | Me | H | F | R,S | HCl | 1.3 |
| 10 | 2 | Me | Me | t-BuO | H | H | H | $CHF_2$ | R | NaHSO4 | 1.6 |
| 11 | 2 | Me | Me | t-BuO | Et | Et | $CH_3$ | $CF_3$ | R | $MeSO_3H$ | 11.2 |
| 12 | 3 | H | H | t-BuO | Me | Et | H | $CF_2CH_3$ | R | HCl | 1.2 |
| 13 | 3 | H | H | t-BuO | Me | Me | H | F | R | $MeSO_3H$ | 15.6 |
| 14 | 5 | H | H | t-BuO | —(CH$_2$)$_2$— | | F | F | | $MeSO_3H$ | 14.3 |
| 15 | 6 | H | Ac | Ph | Me | cyclopentyl | F | $CF_3$ | R,S | $MeSO_3H$ | 15.0 |
| C1 | 2 | H | Ac | Ph | Me | Me | H | F | R | $MeSO_3H$ | 10.5 |
| C2 | 2 | H | Ac | Ph | Me | Me | H | F | S | $MeSO_3H$ | 10.4 |
| C3 | 2 | H | Ac | Ph | Me | Me | H | F | R,S | $MeSO_3H$ | 10.3 |
| C4 | 2 | H | H | t-BuO | Me | Me | H | F | R | $MeSO_3H$ | 12.4 |
| C5 | 2 | H | H | t-BuO | Me | Me | H | F | S | $MeSO_3H$ | 12.7 |

TABLE 2-continued

Solubility of the water soluble taxane derivatives in physiological saline

| Compd. No. | n | $R^6$ | $R^7$ | $R^8$ | $R^9$ | $R^{10}$ | X | Y | C* | A | Solubility (mg/ml) |
|---|---|---|---|---|---|---|---|---|---|---|---|
| C6 | 2 | H | H | t-BuO | Me | Me | H | F | R,S | $MeSO_3H$ | 12.5 |
| C7 | 2 | Me | Me | t-BuO | Me | Me | H | F | R | $MeSO_3H$ | 0.9 |
| C8 | 2 | Me | Me | t-BuO | Me | Me | H | F | S | $MeSO_3H$ | 0.6 |
| C9 | 2 | Me | Me | t-BuO | Me | Me | H | F | R,S | $MeSO_3H$ | 0.4 |

Experimental Example 1.2. In Vitro Dissociation in Rat Blood Plasma of Rat

The obtained water soluble taxane derivatives were formulated as 0.2 mg/ml aqueous solutions. 0.1 ml samples were taken from each of the solutions, added respectively to 0.9 ml of fresh blood plasma (anticoagulated with heparin) from SD rats, homogeneously mixed, and placed in a thermostatic water bath at 37° C. for incubation with time being recorded. After 2 min, 5 min and 10 min of incubation, 0.2 ml of solutions were respectively taken from each of the samples, and added to acetonitrile (0.4 ml) cooled to −20° C. for precipitation of protein. The samples were shaken and centrifuged for 10 min (10,000 rpm), and the supernatant was then taken for HPLC analysis. The results are presented in following Table 3:

Experimental Example 1.3. In Vitro Dissociation in Blood Plasma of Rabbit

The obtained water soluble taxane derivatives were formulated as 0.2 mg/ml aqueous solutions. 0.1 ml samples were taken from each of the solutions, added respectively to 0.9 ml of fresh blood plasma (anticoagulated with heparin) from New Zealand white rabbits, homogeneously mixed, and placed in a thermostatic water bath at 37° C. for incubation with time being recorded. After 5 min, 20 min and 60 min of incubation, 0.2 ml of solutions were respectively taken from each of the samples, and added to acetonitrile (0.4 ml) cooled to −20° C. for precipitation of protein. The samples were shaken and centrifuged for 10 min (10,000 rpm), and the supernatant was then taken for HPLC analysis. The results are presented in following Table 4:

TABLE 3

Test of in vitro dissociation of the water soluble taxane derivatives in blood plasma of rat

| Compd. No. | n | $R^6$ | $R^7$ | $R^8$ | $R^9$ | $R^{10}$ | X | Y | C* | A | Sampling time/dissociation percent (%) 2 min | 5 min | 10 min |
|---|---|---|---|---|---|---|---|---|---|---|---|---|---|
| 01 | 2 | H | Ac | Ph | Me | Me | H | F | R | HCl | 63.5 | 96.8 | 100 |
| 02 | 2 | H | Ac | Ph | Me | Me | H | F | S | HCl | 59.8 | 95.6 | 100 |
| 03 | 2 | H | Ac | Ph | Me | Me | H | F | R, S | HCl | 61.8 | 93.1 | 100 |
| 04 | 2 | H | H | t-BuO | Me | Me | H | F | R | HCl | 58.6 | 92.6 | 100 |
| 05 | 2 | H | H | t-BuO | Me | Me | H | F | S | HCl | 56.4 | 91.1 | 100 |
| 06 | 2 | H | H | t-BuO | Me | Me | H | F | R, S | HCl | 56.4 | 91.1 | 100 |
| 07 | 2 | Me | Me | t-BuO | Me | Me | H | F | R | HCl | 49.5 | 89.6 | 100 |
| 08 | 2 | Me | Me | t-BuO | Me | Me | H | F | S | HCl | 47.6 | 87.6 | 100 |
| 09 | 2 | Me | Me | t-BuO | Me | Me | H | F | R, S | HCl | 47.8 | 89.1 | 100 |
| 10 | 2 | Me | Me | t-BuO | H | H | H | $CHF_2$ | R | $NaHSO_4$ | 45.2 | 86.5 | 96.8 |
| 11 | 2 | Me | Me | t-BuO | Et | Et | $CH_3$ | $CF_3$ | R | $MeSO_3H$ | 52.3 | 89.6 | 97.2 |
| 12 | 3 | H | H | t-BuO | Me | Et | H | $CF_2CH_3$ | R | HCl | 43.6 | 75.6 | 89.6 |
| 13 | 3 | H | H | t-BuO | Me | Me | H | F | R | $MeSO_3H$ | 45.7 | 85.2 | 92.3 |
| 14 | 5 | H | H | t-BuO | —(CH$_2$)$_2$— | | F | F | — | $MeSO_3H$ | 42.1 | 55.7 | 72.5 |
| 15 | 6 | H | Ac | Ph | Me | cyclopentyl | F | $CF_3$ | R, S | $MeSO_3H$ | 35.0 | 46.2 | 57.9 |
| C1 | 2 | H | Ac | Ph | Me | Me | H | F | R | $MeSO_3H$ | 64.3 | 97.0 | 100 |
| C2 | 2 | H | Ac | Ph | Me | Me | H | F | S | $MeSO_3H$ | 62.8 | 96.5 | 100 |
| C3 | 2 | H | Ac | Ph | Me | Me | H | F | R, S | $MeSO_3H$ | 63.7 | 96.8 | 100 |
| C4 | 2 | H | H | t-BuO | Me | Me | H | F | R | $MeSO_3H$ | 59.2 | 93.4 | 100 |
| C5 | 2 | H | H | t-BuO | Me | Me | H | F | S | $MeSO_3H$ | 58.9 | 93.3 | 100 |
| C6 | 2 | H | H | t-BuO | Me | Me | H | F | R, S | $MeSO_3H$ | 59.1 | 93.3 | 100 |
| C7 | 2 | Me | Me | t-BuO | Me | Me | H | F | R | $MeSO_3H$ | 49.7 | 88.9 | 100 |
| C8 | 2 | Me | Me | t-BuO | Me | Me | H | F | S | $MeSO_3H$ | 49.4 | 88.4 | 100 |
| C9 | 2 | Me | Me | t-BuO | Me | Me | H | F | R, S | $MeSO_3H$ | 49.3 | 88.6 | 100 |

TABLE 4

Test of in vitro dissociation of the water soluble taxane derivatives in blood plasma of rabbit

| Compd. No. | n | $R^6$ | $R^7$ | $R^8$ | $R^9$ | $R^{10}$ | X | Y | C* | A | Sampling time/ dissociation percent (%) 5 min | 20 min | 60 min |
|---|---|---|---|---|---|---|---|---|---|---|---|---|---|
| 01 | 2 | H | Ac | Ph | Me | Me | H | F | R | HCl | 76.5 | 98.3 | 100 |
| 02 | 2 | H | Ac | Ph | Me | Me | H | F | S | HCl | 68.2 | 97.5 | 100 |
| 03 | 2 | H | Ac | Ph | Me | Me | H | F | R, S | HCl | 75.7 | 93.5 | 100 |
| 04 | 2 | H | H | t-BuO | Me | Me | H | F | R | HCl | 80.2 | 93.5 | 100 |
| 05 | 2 | H | H | t-BuO | Me | Me | H | F | S | HCl | 79.3 | 91.8 | 100 |
| 06 | 2 | H | H | t-BuO | Me | Me | H | F | R, S | HCl | 75.6 | 98.6 | 100 |
| 07 | 2 | Me | Me | t-BuO | Me | Me | H | F | R | HCl | 79.2 | 95.5 | 100 |
| 08 | 2 | Me | Me | t-BuO | Me | Me | H | F | S | HCl | 89.9 | 93.2 | 100 |
| 09 | 2 | Me | Me | t-BuO | Me | Me | H | F | R, S | HCl | 83.2 | 97.1 | 100 |
| 10 | 2 | Me | Me | t-BuO | H | H | H | $CHF_2$ | R | $NaHSO_4$ | 38.1 | 63.2 | 80.3 |
| 11 | 2 | Me | Me | t-BuO | Et | Et | $CH_3$ | $CF_3$ | R | $MeSO_3H$ | 56.2 | 80.5 | 92.1 |
| 12 | 3 | H | H | t-BuO | Me | Et | H | $CF_2CH_3$ | R | HCl | 35.2 | 61.3 | 73.2 |
| 13 | 3 | H | H | t-BuO | Me | Me | H | F | R | $MeSO_3H$ | 33.2 | 55.8 | 62.1 |
| C1 | 2 | H | Ac | Ph | Me | Me | H | F | R | $MeSO_3H$ | 77.2 | 98.4 | 100 |
| C2 | 2 | H | Ac | Ph | Me | Me | H | F | S | $MeSO_3H$ | 69.7 | 98.1 | 100 |
| C3 | 2 | H | Ac | Ph | Me | Me | H | F | R, S | $MeSO_3H$ | 76.5 | 94.6 | 100 |
| C4 | 2 | H | H | t-BuO | Me | Me | H | F | R | $MeSO_3H$ | 81.6 | 94.8 | 100 |
| C5 | 2 | H | H | t-BuO | Me | Me | H | F | S | $MeSO_3H$ | 81.2 | 93.1 | 100 |
| C6 | 2 | H | H | t-BuO | Me | Me | H | F | R, S | $MeSO_3H$ | 76.8 | 97.8 | 100 |
| C7 | 2 | Me | Me | t-BuO | Me | Me | H | F | R | $MeSO_3H$ | 78.4 | 94.8 | 100 |
| C8 | 2 | Me | Me | t-BuO | Me | Me | H | F | S | $MeSO_3H$ | 85.6 | 94.5 | 100 |
| C9 | 2 | Me | Me | t-BuO | Me | Me | H | F | R, S | $MeSO_3H$ | 81.2 | 96.7 | 100 |

Experimental Example 1.4. Preliminary In Vivo Metabolic Test of the Water Soluble Paclitaxel Derivatives in Rats Method of Study:

12 SD rats (male, body weight: 200-220 g) were randomly divided into four groups, and intravenously administered with 5 mg/kg of compounds 01, 02, 03 and commercially available paclitaxel in a volume of 5 ml/kg, respectively. Compounds 01, 02 and 03 were formulated with 5% dextrose injection (pH=5), and paclitaxel is in the form of a commercially available injection. After 5 min of administration, 0.3 ml of venous blood was taken from the retrobulbar venous plexus of the rats, placed in heparinized tubes, and centrifuged at 11,000 rpm for 5 min. Blood plasma was separated, and the concentrations of the compounds in the blood plasma were determined by liquid chromatography-mass spectrometry.

Result:

After intravenous injection of compounds 01, 02, and 03, compounds 01, 02, and 03 cannot be detected in the blood plasma, and only paclitaxel can be detected.

The mean concentrations (ng/ml) of paclitaxel in the blood plasma of animals from each group were 1789, 1637, 1825, and 1793, respectively.

Experimental Example 1.5. In Vivo Metabolic Test of the Water Soluble Docetaxel Derivatives in Rats Method of Study:

12 SD rats (male, body weight: 200-220 g) were randomly divided into four groups, and intravenously administered with 5 mg/kg of compounds 04, 05, 06 and commercially available docetaxel in a volume of 5 ml/kg, respectively. Compounds 04, 05 and 06 were formulated with 5% dextrose injection (pH=5), and docetaxel is in the form of a commercially available injection. After 5 min of administration, 0.3 ml of venous blood was taken from the retrobulbar venous plexus of the rats, placed in heparinized tubes, and centrifuged at 11,000 rpm for 5 min. Plasma was separated, and the concentrations of the compounds in the plasma were determined by liquid chromatography □-mass spectrometry.

Result:

After intravenous injection of compounds 04, 05, and 06, compounds 04, 05, and 06 cannot be detected in the blood plasma, and only docetaxel can be detected.

The mean concentrations (ng/ml) of docetaxel in the blood plasma of animals from each group were 1506, 1387, 1621, and 769, respectively.

Experimental Example 1.6. Antitumor Activity Test of the Water Soluble Taxane Derivatives 1.6.1. Test of the inhibitory activity of the water soluble paclitaxel derivatives on subcutaneously xenografted tumor of human ovarian cancer SK-OV-3 in nude mice: evaluating and comparing the inhibitory activity of the water soluble paclitaxel derivatives of the present invention, paclitaxel and Abraxane® on subcutaneously xenografted tumor of human ovarian cancer SK-OV-3 in nude mice.

Dosage Regimen and Experimental Procedures:

Human ovarian cancer SK-OV-3 cells were subcutaneously inoculated to nude mice. After the tumor volume reached 100-150 mm³, the animals were randomly divided into groups (D0), and administered with the water soluble paclitaxel derivatives of the present invention, paclitaxel, and Abraxane®, respectively once per day for 5 days. The dosage and dosage regimen are shown in following Table 5. The tumor volume was measured 2-3 times per week, the animals were weighed and the data were recorded until day 22 (D22) after grouping.

The tumor volume (V) was calculated according to the equation: $V=\frac{1}{2} \times a \times b^2$, wherein a and b represent the length and the width, respectively.

$T/C (\%)=(T-T_0)/(C-C_0) \times 100$, wherein T and C represent the tumor volume at the end of the experiment; and $T_0$ and $C_0$ represent the tumor volume at the beginning of the experiment.

The antitumor activity data are shown in following Table 5:

The numbers of mice at the beginning of the experiment: n=10 in the control group, and n=6 in the administered group.

Conclusion: the water soluble paclitaxel derivatives of the present invention have an inhibitory effect on human ovarian cancer SK-OV-3.

1.6.2. Test of the inhibitory activity of the water soluble docetaxel derivatives on subcutaneously xenografted tumor of human prostate cancer PC-3 in nude mice: evaluating and comparing the inhibitory activity of the water soluble docetaxel derivatives and docetaxel on subcutaneously xenografted tumor of human prostate cancer PC-3 in nude mice.

Dosage regimen and experimental procedures:

Human prostate cancer PC-3 cells were subcutaneously inoculated into nude mice. After the tumor volume reached 100-150 mm$^3$, the animals were randomly divided into several groups, and administered with the water soluble docetaxel derivatives of the present invention and docetaxel, respectively once on the same day (D0). The dosage and dosage regimen are shown in following Table 6. The tumor

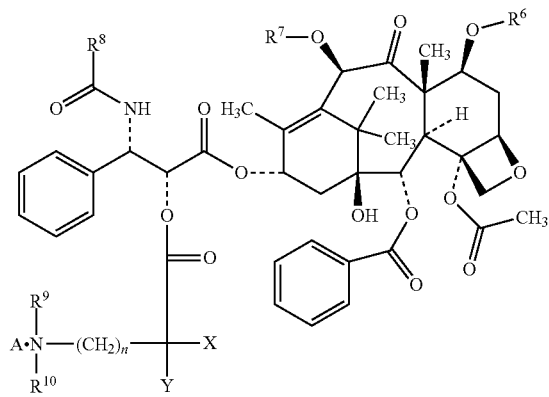

TABLE 5

The inhibitory activity of the water soluble paclitaxel derivatives, paclitaxel and Abraxane ® on subcutaneously xenografted tumor of human ovarian cancer SK-OV-3 in nude mice.

| Compd. No. | Dosage | Time and route of administration | n | $R^6$ | $R^7$ | $R^8$ | $R^9$ | $R^{10}$ | X | Y | C* | A |
|---|---|---|---|---|---|---|---|---|---|---|---|---|
| the control group | — | D0-4 IV | — | — | — | — | — | — | — | — | — | — |
| paclitaxel | 16 mg/kg | D0-4 IV | — | — | — | — | — | — | — | — | — | — |
| Abraxane ® | 24 mg/kg | D0-4 IV | — | — | — | — | — | — | — | — | — | — |
| C1 | 24 mg/kg | D0-4 IV | 2 | H | Ac | Ph | Me | Me | H | F | R | MeSO$_3$H |
| C2 | 24 mg/kg | D0-4 IV | 2 | H | Ac | Ph | Me | Me | H | F | S | MeSO$_3$H |
| C3 | 24 mg/kg | D0-4 IV | 2 | H | Ac | Ph | Me | Me | H | F | R, S | MeSO$_3$H |
| 16 | 24 mg/kg | D0-4 IV | 2 | H | Ac | Ph | Et | Me | H | F | R | MeSO$_3$H |
| 17 | 24 mg/kg | D0-4 IV | 2 | H | Ac | Ph | Et | Et | H | F | S | fumaric acid |
| 18 | 24 mg/kg | D0-4 IV | 2 | H | Ac | Ph | Me | i-Pro | H | F | R, S | HCl |
| 19 | 24 mg/kg | D0-4 IV | 2 | H | Ac | Ph | Me | Me | H | CF$_3$ | R, S | p-toluene sulfonic acid |
| 20 | 24 mg/kg | D0-4 IV | 2 | H | Ac | Ph | Me | Me | H | CHF$_2$ | R, S | HCl |
| 21 | 24 mg/kg | D0-4 IV | 3 | H | Ac | Ph | Me | Me | H | F | R | maleic acid |
| 22 | 24 mg/kg | D0-4 IV | 4 | H | Ac | Ph | Me | Me | H | CHF$_2$ | S | sulfuric acid |

| Compd. No. | Tumor volume (mm$^3$) (D0) | Tumor volume (mm$^3$) (D22) | T/C (%) D22 | Tumor inhibitory percent (%)$^\Delta$ D22 | Weight change (%) D4 |
|---|---|---|---|---|---|
| the control group | 134.6 ± 18.3 | 980.4 ± 271.9 | — | — | −11 |
| paclitaxel | 134.6 ± 19.7 | 53.7 ± 11.2 | −60 | 160 | −4.8 |
| Abraxane ® | 126.0 ± 10.7 | 53.8 ± 13.9 | −57 | 157 | −8.2 |
| C1 | 133.6 ± 9.5 | 49.8 ± 10.4 | −63 | 163 | −5.9 |
| C2 | 134.3 ± 10.4 | 51.2 ± 11.2 | −61 | 158 | −5.8 |
| C3 | 133.4 ± 10.4 | 50.6 ± 9.7 | −64 | 165 | −6.0 |
| 16 | 133.6 ± 9.4 | 55.7 ± 10.6 | −53 | 137 | −7.0 |
| 17 | 133.6 ± 9.4 | 55.7 ± 10.1 | −44 | 114 | −8.1 |
| 18 | 127.9 ± 11.4 | 60.4 ± 12.3 | −38 | 98 | −10.3 |
| 19 | 134.9 ± 11.4 | 57.3 ± 11.4 | −48 | 124 | −8.9 |
| 20 | 133.4 ± 12.6 | 61.2 ± 13.5 | −35 | 91 | −8.4 |
| 21 | 135.8 ± 14.7 | 70.8 ± 16.8 | −23 | 60 | −9.4 |
| 22 | 133.8 ± 12.2 | 79.8 ± 12.8 | −14 | 36 | −11.6 |

The structures of the compounds administered are represented by the above formula and the substituents listed in above Table 5.

D0: the time of administration for the first time;

Δ: $P_{(D22)}$=0.000, compared to the control, using Student's t-test.

volume was measured 2-3 times per week, the animals were weighed and the data were recorded until day 20 (D20) after grouping.

The tumor volume (V) was calculated according to the equation: $V=\frac{1}{2} \times a \times b^2$, wherein a and b represent the length and the width, respectively.

T/C (%)=(T−T$_0$)/(C−C$_0$)×100, wherein T and C represent the tumor volume at the end of the experiment; and T$_0$ and C$_0$ represent the tumor volume at the beginning of the experiment.

The antitumor activity data are shown in following Table 6:

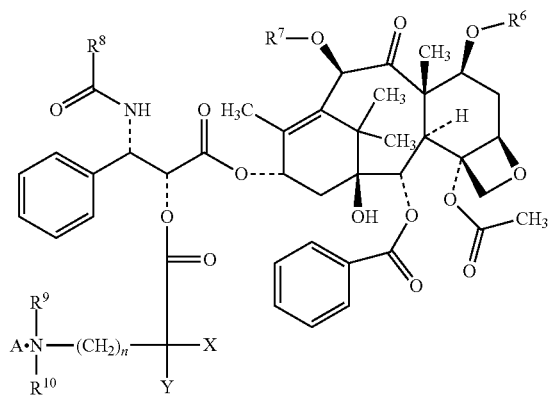

D0: the time of administration for the first time; Δ: P$_{(D20)}$=0.000, compared to the control, using Student's t-test.

The numbers of mice at the beginning of the experiment: n=10 in the control group, and n=6 in the administered group.

Conclusion: the water soluble docetaxel derivatives of the present invention have an inhibitory effect on human prostate cancer PC-3.

1.6.3. Test of the inhibitory activity of the water soluble cabazitaxel derivatives on subcutaneously xenografted tumor of human prostate cancer PC-3 in nude mice: evaluating and comparing the inhibitory activity of the water soluble cabazitaxel derivatives and cabazitaxel on subcutaneously xenografted tumor of human prostate cancer PC-3 in nude mice.

Dosage Regimen and Experimental Procedures:

Human prostate cancer PC-3 cells were subcutaneously inoculated into nude mice. After the tumor volume reached 100-150 mm$^3$, the animals were randomly divided into several groups, and administered with the water soluble cabazitaxel derivatives of the present invention and cabazitaxel, respectively once on the same day (D0). The dosage and dosage regimen are shown in following table 7. The

TABLE 6

The inhibitory activity of the water soluble docetaxel derivatives and docetaxel on subcutaneously xenografted tumor of human prostate cancer PC-3 in nude mice

| Compd. No. | Dosage | Time and route of administration | n | R$^6$ | R$^7$ | R$^8$ | R$^9$ | R$^{10}$ | X | Y | C* | A |
|---|---|---|---|---|---|---|---|---|---|---|---|---|
| the control group | — | D0 IV | — | — | — | — | — | — | — | — | — | — |
| docetaxel | 14 mg/kg | D0 IV | — | — | — | — | — | — | — | — | — | — |
| C4 | 33.6 mg/kg | D0 IV | 2 | H | H | t-BuO | Me | Me | H | F | R | MeSO$_3$H |
| C5 | 33.6 mg/kg | D0 IV | 2 | H | H | t-BuO | Me | Me | H | F | S | MeSO$_3$H |
| C6 | 33.6 mg/kg | D0 IV | 2 | H | H | t-BuO | Me | Me | H | F | R, S | MeSO$_3$H |
| 23 | 33.6 mg/kg | D0 IV | 2 | H | H | t-BuO | Et | Me | H | F | R | MeSO$_3$H |
| 24 | 33.6 mg/kg | D0 IV | 2 | H | H | t-BuO | Et | Et | H | F | S | maleic acid |
| 25 | 33.6 mg/kg | D0 IV | 2 | H | H | t-BuO | Me | i-Pro | H | F | R | HCl |
| 26 | 33.6 mg/kg | D0 IV | 2 | H | H | t-BuO | Me | Me | H | CF$_3$ | R | MeSO$_3$H |
| 27 | 33.6 mg/kg | D0 IV | 2 | H | H | t-BuO | Me | Me | H | CHF$_2$ | R, S | HCl |
| 28 | 33.6 mg/kg | D0 IV | 3 | H | H | t-BuO | Me | Me | H | F | R, S | MeSO$_3$H |
| 29 | 33.6 mg/kg | D0 IV | 4 | H | H | t-BuO | Me | Me | H | F | S | sulfuric acid |

| Compd. No. | Tumor volume (mm$^3$) (D0) | Tumor volume (mm$^3$) (D20) | T/C (%) D20 | Tumor inhibitory percent (%)$^\Delta$ D20 | Weight change (%) D6 |
|---|---|---|---|---|---|
| the control group | 110.5 ± 4.4 | 870.5 ± 60.5 | — | — | −16 |
| docetaxel | 111.5 ± 1.3 | 81.4 ± 25.1 | −27 | 127 | −12.3 |
| C4 | 113.7 ± 2.9 | 26.6 ± 12.4 | −77 | 177 | −12.5 |
| C5 | 113.4 ± 3.1 | 26.8 ± 12.6 | −76 | 175 | −12.4 |
| C6 | 113.8 ± 3.0 | 27.0 ± 12.3 | −76 | 175 | −12.6 |
| 23 | 113.8 ± 3.0 | 30.4 ± 11.1 | −62 | 143 | −13.6 |
| 24 | 114.4 ± 2.8 | 32.4 ± 13.5 | −52 | 120 | −14.1 |
| 25 | 116.3 ± 3.7 | 35.3 ± 14.7 | −44 | 101 | −14.4 |
| 26 | 113.5 ± 2.8 | 34.5 ± 12.6 | −46 | 105 | −13.9 |
| 27 | 116.7 ± 3.1 | 36.8 ± 13.4 | −37 | 85 | −15.1 |
| 28 | 118.2 ± 4.8 | 41.5 ± 14.7 | −28 | 64 | −15.4 |
| 29 | 114.7 ± 3.5 | 52.4 ± 12.5 | −20 | 45 | −15.8 |

The structures of the compounds administered are shown by the above formula and the substituents listed in above Table 6;

tumor volume was measured 2-3 times per week, the animals were weighed and the data were recorded until day 20 (D20) after grouping.

The tumor volume (V) was calculated according to the equation: $V=\frac{1}{2}\times a\times b^2$, wherein a and b represent the length and the width, respectively.

$T/C\ (\%)=(T-T_0)/(C-C_0)\times 100$, wherein T and C represent the tumor volume at the end of the experiment; and $T_0$ and $C_0$ represent the tumor volume at the beginning of the experiment.

The antitumor activity data are shown in following Table 7:

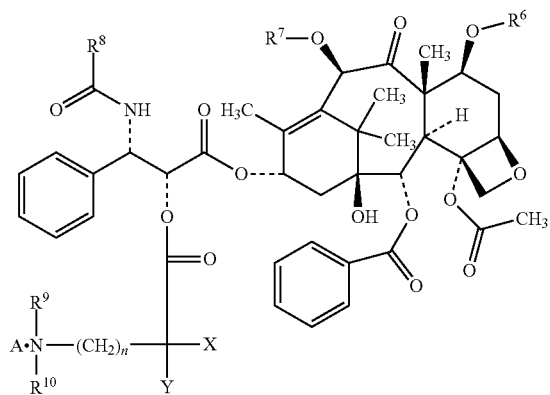

The structures of the compounds administered are shown by the above formula and the substituents listed in above Table 7;

D0: the time of administration for the first time;

Δ: $P_{(D20)}=0.000$, compared to the control, using Student's t-test.

The numbers of mice at the beginning of the experiment: n=10 in the control group, and n=6 in the administered group.

Conclusion: the water soluble cabazitaxel derivatives of the present invention have an inhibitory effect on human prostate cancer PC-3.

Experimental Example 2

Examples of the carboxylic acid derivative of the present invention for the preparation of a water soluble propofol prodrug:

The carboxylic acid derivatives of the present invention can be used for the preparation of water soluble propofol derivatives. The general formulae of such water soluble propofol derivatives are as follows. The serial numbers and characterization data thereof are as shown in following Table 8:

TABLE 7

The inhibitory activity of the water soluble cabazitaxel derivatives and cabazitaxel on subcutaneously xenografted tumor of human prostate cancer PC-3 in nude mice

| Compd. No. | Dosage | Time and route of administration | n | $R^6$ | $R^7$ | $R^8$ | $R^9$ | $R^{10}$ | X | Y | C* | A |
|---|---|---|---|---|---|---|---|---|---|---|---|---|
| the control group | — | D0 IV | — | — | — | — | — | — | — | — | — | — |
| cabazitaxel | 7 mg/kg | D0 IV | — | — | — | — | — | — | — | — | — | — |
| C7 | 13 mg/kg | D0 IV | 2 | Me | Me | t-BuO | Me | Me | H | F | R | MeSO$_3$H |
| C8 | 13 mg/kg | D0 IV | 2 | Me | Me | t-BuO | Me | Me | H | F | S | MeSO$_3$H |
| C9 | 13 mg/kg | D0 IV | 2 | Me | Me | t-BuO | Me | Me | H | F | R, S | MeSO$_3$H |
| 30 | 13 mg/kg | D0 IV | 2 | Me | Me | t-BuO | Et | Me | H | F | R | maleic acid |
| 31 | 13 mg/kg | D0 IV | 2 | Me | Me | t-BuO | Et | Et | H | F | R | MeSO$_3$H |
| 32 | 13 mg/kg | D0 IV | 2 | Me | Me | t-BuO | Me | i-Pro | H | F | R | HCl |
| 33 | 13 mg/kg | D0 IV | 2 | Me | Me | t-BuO | Me | Me | H | CF$_3$ | R | MeSO$_3$H |
| 34 | 13 mg/kg | D0 IV | 2 | Me | Me | t-BuO | Me | Me | H | CHF$_2$ | R | p-toluene sulfonic acid |
| 35 | 13 mg/kg | D0 IV | 3 | Me | Me | t-BuO | Me | Me | H | F | R | HCl |
| 36 | 13 mg/kg | D0 IV | 4 | Me | Me | t-BuO | Me | Me | H | F | R | sulfuric acid |

| | Anti-tumor activity data | | | | |
|---|---|---|---|---|---|
| Compd. No. | Tumor volume (mm³) (D0) | Tumor volume (mm³) (D20) | T/C (%) D20 | Tumor inhibitory percent (%)$^\Delta$ D20 | Weight change (%) D6 |
| the control group | 111.3 ± 3.8 | 868.4 ± 58.7 | — | — | −17 |
| cabazitaxel | 111.7 ± 1.8 | 79.9 ± 24.8 | −27 | 127 | −13.8 |
| C7 | 111.5 ± 2.2 | 31.5 ± 11.8 | −67 | 154 | −14.2 |
| C8 | 111.9 ± 2.0 | 32.1 ± 12.1 | −66 | 151 | −14.4 |
| C9 | 111.4 ± 2.3 | 32.5 ± 11.6 | −66 | 151 | −14.4 |
| 30 | 112.4 ± 3.0 | 35.8 ± 12.7 | −56 | 128 | −14.7 |
| 31 | 112.0 ± 2.4 | 38.6 ± 13.4 | −50 | 114 | −15.1 |
| 32 | 111.7 ± 3.2 | 42.8 ± 11.9 | −45 | 101 | −15.4 |
| 33 | 110.2 ± 4.6 | 42.3 ± 12.6 | −46 | 105 | −15.8 |
| 34 | 116.7 ± 3.9 | 48.4 ± 14.7 | −37 | 85 | −16.1 |
| 35 | 112.9 ± 4.4 | 55.3 ± 13.8 | −28 | 64 | −16.6 |
| 36 | 111.9 ± 3.7 | 66.8 ± 12.4 | −20 | 46 | −16.8 |

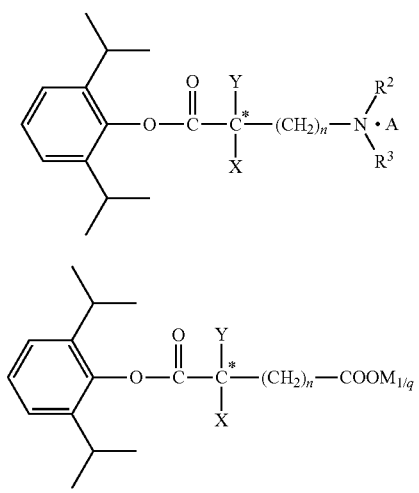

(E)

(F)

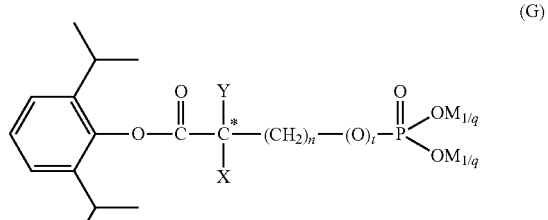

(G)

TABLE 8

The serial numbers and characterization data of the water soluble propofol prodrugs prepared from the carboxylic acid derivatives of the present invention

| Compd. No. | Compound Name | Mass spectrometry data |
|---|---|---|
| E1 | propofol 4-(N,N-dimethyl)amino-2(R,S)-fluorobutyrate hydrochloride | 310.1 |
| E2 | propofol 4-(N,N-dimethyl)amino-2(R)-fluorobutyrate hydrochloride | 310.1 |
| E3 | propofol 4-(N,N-dimethyl)amino-2(R)-2-trifluoromethylbutyrate hydrochloride | 360.18 |
| E4 | propofol 4-(N-methyl-N-ethyl)amino-2(R,S)-2-fluorobutyrate hydrochloride | 324.21 |
| E5 | propofol 5-(N-methyl-N-benzyl)amino-2(S)-2-fluorovalerate hydrochloride | 400.24 |
| E6 | propofol 3-(N-isopropyl)amino-2(R,S)-2-monofluoromethylpropionate methanesulfonate | 324.22 |
| E7 | propofol 4-N-(aziridin-1-yl)-2(S)-2-fluorobutyrate hydrochloride | 308.15 |
| E8 | propofol 4-(pyrrolidin-1-yl)-2(R)-2-fluorobutyrate hydrochloride | 336.19 |
| F1 | propofol 4-carboxyl-2(R,S)-fluorovalerate sodium salt | 309.14 |
| F2 | propofol 4-carboxyl-2(S)-fluorovalerate potassium salt | 309.11 |
| F3 | propofol 4-carboxyl-2(R)-2-trifluoromethyl valerate lithium salt | 359.11 |
| F4 | di[propofol 7-carboxyl-2(R,S)-fluorocaprylate] calcium salt | 351.14 |
| F5 | di[propofol 5-carboxyl-2(S)-fluorohexanoate] zinc salt | 323.12 |
| F6 | tri[propofol 8-carboxyl-2(R,S)-monofluoromethylpelargonate] aluminium salt | 379.18 |
| F7 | propofol 3-carboxyl-2(R)-fluorobutyrate sodium salt | 295.11 |
| F8 | propofol 2-carboxyl-2(S)-fluoropropionate sodium salt | 281.09 |
| G1 | {1-[4-(2,6-diisopropylphenoxy)-4-oxo-3-(R,S)-3-fluoro-1-butyl]} phosphate monoester dipotassium salt | 361.13 |
| G2 | {1-[4-(2,6-diisopropylphenoxy)-4-oxo-3-(S)-3-fluoro-1-butyl]} phosphate monoester disodium salt | 361.13 |
| G3 | {1-[4-(2,6-diisopropylphenoxy)-4-oxo-3-(R)-3-trifluoromethyl-1-butyl]} phosphate monoester dilithium salt | 411.13 |
| G4 | propofol 4-phosphoryl-2(R,S)-fluorobutyrate calcium salt | 345.13 |
| G5 | propofol 5-phosphoryl-2(S)-fluorovalerate zinc salt | 359.15 |
| G6 | tri[propofol 3-phosphoryl-2(R,S)-2-monofluoromethylpropionate] dialuminum salt | 345.16 |

Experimental Example 2.1. Test of In Vitro Dissociation of the Water Soluble Propofols in Blood Plasma The obtained water soluble propofol derivatives were formulated as 1 mg/ml solutions in physiological saline. 0.1 ml samples were taken from each of the solutions, added respectively to 1 ml of blood plasma of rabbit (taken from New Zealand white rabbits, treated according to conventional methods, anticoagulated with heparin) or 1 ml of blood plasma of rat (taken from live SD rats, treated according to conventional methods, anticoagulated with heparin), homogeneously mixed, and placed in a thermostatic water bath at 37° C. for incubation with time being recorded. Samples were taken at different time points after the experiment began, and 2 ml of acetonitrile was immediately added. The samples were shaken and centrifuged for 5 min (15,000 rpm), and the supernatant was then taken for HPLC analysis. The results are presented as follows:

TABLE 9

In vitro dissociation percent of amino acid-based propofol derivatives of formula E in blood plasma

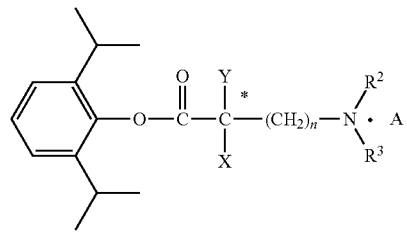

(E)

| E | n | $R^2$ | $R^3$ | X | Y | C* | A | Plasma | 5 s | 15 s | 30 s |
|---|---|---|---|---|---|---|---|---|---|---|---|
| E1 | 2 | Me | Me | H | F | R, S | HCl | Rabbit | | 67.5 | 85.5 |
| | | | | | | | | Rat | 75.1 | 83.2 | 96.7 |
| E2 | 2 | Me | Me | H | F | R | HCl | Rabbit | | 97.7 | 100 |
| | | | | | | | | Rat | 100 | | |
| E3 | 2 | Me | Me | H | $CF_3$ | R | HCl | Rabbit | | 51.7 | 67.2 |
| | | | | | | | | Rat | 77.5 | | |
| E4 | 2 | Me | Et | H | F | R, S | HCl | Rabbit | | 58.3 | 70.4 |
| | | | | | | | | Rat | 70.2 | | |
| E5 | 3 | Me | Bn | H | F | S | HCl | Rabbit | | 48.4 | 69.7 |
| | | | | | | | | Rat | 72.3 | 97.3 | |
| E6 | 1 | H | i-Pro | H | $CH_2F$ | R, S | $MeSO_3H$ | Rabbit | | 27.1 | 44.3 |
| | | | | | | | | Rat | 24.2 | 40.1 | |
| E7 | 2 | $CH_2$—$CH_2$ | | H | F | S | HCl | Rabbit | | 89.4 | 94.4 |
| | | | | | | | | Rat | 92.3 | | |
| E8 | 2 | $CH_2CH_2CH_2CH_2$ | | H | F | R | HCl | Rabbit | | 91.1 | 98.2 |
| | | | | | | | | Rat | 95.6 | | |

TABLE 10

In vitro dissociation percent of diacid monoester-based propofol derivatives of formula F in blood plasma

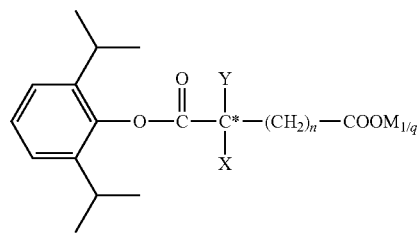

(F)

| F | n | M | t | X | Y | C* | Plasma | 5 s | 15 s | 30 s |
|---|---|---|---|---|---|---|---|---|---|---|
| F1 | 2 | Na | 1 | H | F | R, S | Rabbit | | 47.5 | 75.5 |
| | | | | | | | Rat | 64.1 | 70.2 | 86.7 |

TABLE 10-continued

In vitro dissociation percent of diacid monoester-based propofol derivatives of formula F in blood plasma

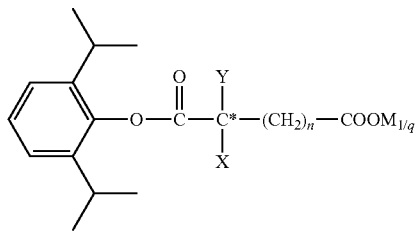

(F)

| F | n | M | t | X | Y | C* | Plasma | 5 s | 15 s | 30 s |
|---|---|---|---|---|---|----|--------|-----|------|------|
| F2 | 2 | K | 1 | H | F | S | Rabbit |  | 73.4 | 94.8 |
|    |   |   |   |   |   |   | Rat | 92.3 |  |  |
| F3 | 2 | Li | 1 | H | $CF_3$ | R | Rabbit |  | 28.4 | 47.9 |
|    |   |   |   |   |   |   | Rat | 47.4 |  |  |
| F4 | 5 | Ca | 2 | H | F | R, S | Rabbit |  | 48.3 | 61.7 |
|    |   |   |   |   |   |   | Rat | 63.8 |  |  |
| F5 | 3 | Zn | 2 | H | F | S | Rabbit |  | 34.9 | 58.8 |
|    |   |   |   |   |   |   | Rat | 63.2 | 80.3 |  |
| F6 | 6 | Al | 3 | H | $CH_2F$ | R, S | Rabbit |  | 37.1 | 58.3 |
|    |   |   |   |   |   |   | Rat | 34.2 | 55.7 |  |
| F7 | 1 | Na | 1 | H | F | R | Rabbit |  | 46.3 | 72.8 |
|    |   |   |   |   |   |   | Rat | 58.8 | 71.3 | 85.4 |
| F8 | 0 | Na | 1 | H | F | S | Rabbit |  | 41.2 | 70.4 |
|    |   |   |   |   |   |   | Rat | 55.5 | 69.3 | 83.3 |

TABLE 11

In vitro dissociation percent of organic phosphate-based propofol derivatives of formula G in blood plasma

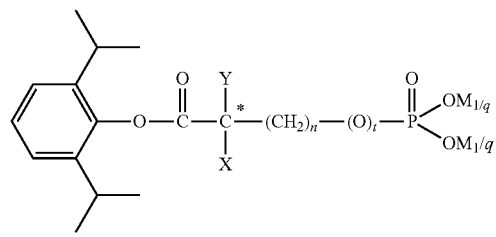

(G)

| G | n | t | M | q | X | Y | C* | Plasma | 5 S | 15 S | 30 S |
|---|---|---|---|---|---|---|----|--------|-----|------|------|
| G1 | 2 | 1 | K | 1 | H | F | R, S | Rabbit |  | 43.7 | 68.7 |
|    |   |   |   |   |   |   |   | Rat | 54.1 | 67.4 | 86.9 |
| G2 | 2 | 1 | Na | 1 | H | F | S | Rabbit |  | 37.2 | 54.3 |
|    |   |   |   |   |   |   |   | Rat | 48.5 | 69.7 |  |
| G3 | 2 | 1 | Li | 1 | H | $CF_3$ | R | Rabbit |  | 21.7 | 43.6 |
|    |   |   |   |   |   |   |   | Rat | 38.7 |  |  |
| G4 | 2 | 0 | Ca | 2 | H | F | R, S | Rabbit |  | 43.3 | 54.8 |
|    |   |   |   |   |   |   |   | Rat | 47.2 |  |  |
| G5 | 3 | 0 | Zn | 2 | H | F | S | Rabbit |  | 33.8 | 56.3 |
|    |   |   |   |   |   |   |   | Rat | 32.9 | 57.6 |  |
| G6 | 1 | 0 | Al | 3 | H | $CH_2F$ | R, S | Rabbit |  | 27.1 | 44.3 |
|    |   |   |   |   |   |   |   | Rat | 22.1 | 39.7 |  |

Experimental Example 2.2. Pharmacodynamic Test of the Water Soluble Propofol Derivatives (Compounds E2, F1, F7, and G2 were Chosen to be Tested)

2.2.1. Test Samples and Administration:

An appropriate amount of test compounds (E2, F1, F7, and G2) were weighed out, and a certain amount of physiological saline was added thereto, so as to form 3 mg/ml or 6 mg/ml solutions, which were then sonicated to dissolve the compounds. Test samples for the experiment on rabbit were formulated to have corresponding concentrations based on the results from a preliminary test. As a control, a fat emulsion injection of propofol (commercially available, 10 mg/ml) was diluted to 3 mg/ml with physiological saline. Rats and mice were administered with samples having a fixed concentration of drugs, while the volume of administration altered according to actual situation. The volume of administration to rabbits was 1 mL/kg body weight.

2.2.2. $ED_{50}$ and $LD_{50}$ Test of the Compounds:

$ED_{50}$ and $LD_{50}$ values concerning anesthesia were determined using a sequential method. Healthy KM mice (male), SD rats (male) and New Zealand White rabbits were used for test. For rats and mice, the compounds were administered by injection at a constant rate via caudal vein for 10 seconds. For rabbits, the compounds were administered by injection at a constant rate via ear vein for 30 seconds. Before the test, a preliminary test was conducted to determine an approximate dosage (volume of administration) that leads to anesthetization (or death) of animals, which was set as the middle dosage in the formal test. 2-3 Dosage groups were set above and below the middle dosage group with an interval of 0.8. The disappearance of righting reflex or death was used as indicators of pharmacological efficacy or toxicity, respectively. The formal test began with the administration of the middle dosage. If animals were anesthetized, a lower dosage was administered; if animals were not anesthetized, a higher dosage was administered, until the cycle was repeated for 3-4 times. $LD_{50}$ and $ED_{50}$ were calculated by a sequential method aot425 software. TI was calculated according to the following equation: $TI = LD_{50}/ED_{50}$.

2.2.3. Determination of the Latent Period and Persistent Period of Anesthesia of the Compounds Kunming mice (male, 5 per group) were administered with the test compounds via intravenous injection at a constant rate for 10 seconds. The periods during which the righting reflex of mice disappeared (latent period) and recovered (persistent period) were recorded.

2.2.4. Test Results 2.2.4.1. Test Results of $LD_{50}/ED_{50}$ and TI Index of the Compounds in Rats/Mice. The Test Results are Shown in Following Table 12:

TABLE 12

Test results of $LD_{50}/ED_{50}$ and TI index of the compounds in rats/mice (n = 10-20)

| Compd. No. and Concentration | Mouse | | Rat | | TI | |
|---|---|---|---|---|---|---|
| | $LD_{50}$ (mg/kg) | $ED_{50}$ (mg/kg) | $LD_{50}$ (mg/kg) | $ED_{50}$ (mg/kg) | Mouse | Rat |
| E2 (3 mg/ml) | 71.8 (51.1-150)* 46.9 (41.3-59.9) | 17.9 (13.7-21.9)* 15.4 (11.7-21.7) | 37.5 (30.9-40.9) | 9.8 (8.3-11.7) | 4* 3 | 3.8 |
| E2 (6 mg/ml) | 55.1 (42.4-67.8)* 48.0 (43.6-51.2) | 15.2 (7.4-20.6)* 13.0 (11.8-15.7) | 30.7 (28.3-36.2) | 10.1 (9.3-12.3) | 3.6* 3.7 | 3.1 |
| F1 (3 mg/ml) | 63.4 (48.7-138.4)* 52.3 (42.5-56.4) | 20.8 (15.6-22.7)* 18.6 (15.4-21.8) | 44.1 (39.3-47.2) | 14.6 (10.2-16.7) | 3* 2.8 | 3.0 |
| F1 (6 mg/ml) | 49.7 (33.7-64.2)* 55.4 (51.8-58.3) | 18.2 (15.3-23.4)* 16.7 (14.4-18.8) | 42.3 (39.6-44.2) | 11.3 (9.5-13.4) | 2.7* 3.3 | 3.7 |
| F7 (3 mg/ml) | 59.8 (50.3-135.9)* 51.6 (41.2-57.4) | 21.4 (17.1-23.8)* 19.2 (17.3-22.8) | 47.4 (41.5-51.7) | 15.7 (12.1-18.9) | 2.8* 2.6 | 3.0 |
| F7 (6 mg/ml) | 51.2 (35.3-65.8)* 56.6 (53.4-60.4) | 20.7 (15.9-26.7)* 18.1 (14.9-21.3) | 44.2 (40.7-47.2) | 12.5 (10.3-14.8) | 2.4* 3.1 | 3.5 |
| G2 (3 mg/ml) | 65.7 (49.4-141.2)* 60.4 (56.4-62.3) | 23.7 (15.6-32.3)* 19.8 (18.4-21.5) | 55.4 (52.7-57.1) | 16.7 (14.2-18.3) | 2.8* 3.0 | 3.3 |
| G2 (6 mg/ml) | 48.7 (38.7-67.2)* 53.6 (60.2-66.3) | 25.6 (14.3-29.8)* 22.8 (17.8-22.3) | 60.1 (58.2-62.4) | 21.1 (19.2-23.4) | 1.9* 2.3 | 2.8 |
| propofol (3 mg/ml) | 38.4 (29.2-54.3) | 7.9 (6.5-9.6) | 21.5 (19.2-24) | 3.91 (0.6-5.5) | 4.9 | 5.5 |
| propofol (6 mg/ml) | 42.9 (38.4-48.0) | 11.3 (10.1-12.6) | 17.4 (16.1-18.4) | 3.5 (0.4-4.3) | 3.8 | 4.9 |

Values marked with * are data from the first test. The remaining data are from the confirmation test.

2.2.4.2. Test Results of $LD_{50}/ED_{50}$ and TI Index of the Compounds in Rabbits. The Test Results are Shown in Following Table 13:

TABLE 13

Test results of $LD_{50}/ED_{50}$ and TI index of the compounds in rabbits

| Compd. No. | $LD_{50}$ (mg/kg) | $ED_{50}$ (mg/kg) | TI index |
|---|---|---|---|
| E2 | 28 (23.0-34.2) | 8 (5.7-10.5) | 3.5 |
| F1 | 34.4 (32.1-36.5) | 12.2 (10.6-14.6) | 2.8 |
| F7 | 36.7 (33.8-39.4) | 13.9 (11.1-16.8) | 2.6 |
| G2 | 38.7 (35.1-41.3) | 14.7 (12.6-19.1) | 2.6 |

2.2.4.3. Test Results of the Latent Period and Persistent Period of Anesthesia of the Compounds in Mice. The Test Results are Shown in Following Table 14:

TABLE 14

Test results of the latent period and persistent period of anesthesia of the compounds in mice (mice, mg/kg, n = 10)

| Compd. No. | Dosage (mg/kg) | Latent Period (s) | Persistent period (s) |
|---|---|---|---|
| E2 (3 mg/ml) | 36 (2 * $ED_{50}$) | 14.6 ± 0.9 | 383.6 ± 242.1 |
| E2 (6 mg/ml) | 30 (2 * $ED_{50}$) | 14.2 ± 1.9 | 543 ± 231 |
| F1 (3 mg/ml) | 42 (2 * $ED_{50}$) | 18.6 ± 0.7 | 349.7 ± 229.4 |
| F1 (6 mg/ml) | 36 (2 * $ED_{50}$) | 15.2 ± 1.4 | 523 ± 248 |
| F7 (3 mg/ml) | 43 (2 * $ED_{50}$) | 20.2 ± 0.6 | 335.5 ± 218.1 |
| F7 (6 mg/ml) | 41 (2 * $ED_{50}$) | 16.2 ± 2.2 | 517 ± 231 |
| G2 (3 mg/ml) | 47 (2 * $ED_{50}$) | 16.3 ± 0.8 | 383.6 ± 242.1 |
| G2 (6 mg/ml) | 51 (2 * $ED_{50}$) | 15.7 ± 2.3 | 571 ± 173 |
| Propofol (3 mg/ml) | 25 (2 * $ED_{50}$) | 8.4 ± 1.1 | 324.8 ± 98.9 |

Conclusion: the water soluble propofol derivatives of the present invention achieve a rapid onset of anesthesia and a short persistent period.

The present invention achieves the following beneficial effects:

As demonstrated by the above test results, the carboxylic acid derivative of the present invention (including the compound of formula I, II or III as well as any specific compound described in the present invention) can form an ester by reacting with a hydroxyl group in a poorly soluble drug through chemical processes to increase the water solubility of the poorly soluble drug, so as to obtain a water soluble prodrug suitable for injection. Surprisingly, the prodrug thus obtained can be easily dissociated in vivo to release the parent drug, without affecting the physiological activity of the prodrug. As a result, the side effects caused by a high molecular co-solvent in an injection of the parent drug can be reduced. The $LD_{50}$ of the compound in mice is above 1,500 mg/kg. That is, the carboxylic acid derivative of the present invention is a suitable ligand for preparing a prodrug.

What is claimed is:

1. A carboxylic acid derivative of general formula (I), (II) or (III):

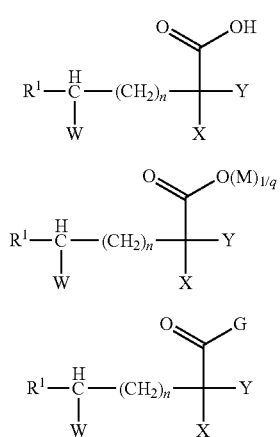

wherein,
$R^1$ is H, methyl, ethyl, n-propyl, or isopropyl;
X is F;
Y is H or F;
n is 1, 2, 3, 4, 5 or 6;
W is $W^1$;
$W^1$ is $.NR^2R^3.A$ or

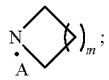

$R^2$ is H, $C_1$-$C_6$ alkyl, cyclopentyl, or cyclohexyl;
$R^3$ is $C_1$-$C_6$ alkyl, cyclopentyl, cyclohexyl, or benzyl;
m is 0, 1, 2 or 3;
A is an acid;
M is a metal ion;
q is the charge number of M; and
G is Cl, Br or benzenesulfonyloxy optionally substituted with alkyl.

2. The carboxylic acid derivative according to claim 1, characterized in that the metal ion is an alkali metal ion, an alkaline earth metal ion or a trivalent metal ion.

3. The carboxylic acid derivative according to claim 2, characterized in that the alkali metal ion is a potassium ion or a sodium ion.

4. The carboxylic acid derivative according to claim 2, characterized in that the alkaline earth metal ion is a magnesium ion, a zinc ion or a calcium ion.

5. The carboxylic acid derivative according to claim 2, characterized in that the trivalent metal ion is an aluminum ion or an iron ion.

6. The carboxylic acid derivative according to claim 1, characterized in that each instance of alkyl is $C_{1-6}$ alkyl.

7. The carboxylic acid derivative according to claim 1, characterized in that the $C_{1-6}$ alkyl is methyl, ethyl, propyl, isopropyl, butyl or isobutyl.

8. The carboxylic acid derivative according to claim 1, characterized in that G is

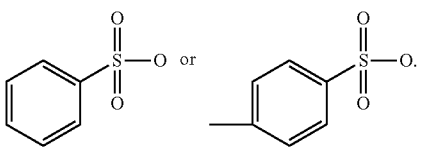

9. The carboxylic acid derivative according to claim 1, characterized in that $R^2$ is H, methyl, ethyl, n-propyl, isopropyl, cyclopentyl, or cyclohexyl, and
$R^3$ is methyl, ethyl, n-propyl, isopropyl, cyclopentyl, cyclohexyl, or benzyl.

10. The carboxylic acid derivative according to claim 1, characterized in that the acid A is an acid which can form a salt with an amine.

11. The carboxylic acid derivative according to claim 1, characterized in that the acid A is hydrochloric acid, hydrobromic acid, sulfuric acid, phosphoric acid, trifluoroacetic acid, difluoroacetic acid, fluoroacetic acid, acetic acid, benzensulfonic acid or p-toluene sulfonic acid.

12. The carboxylic acid derivative according to claim 1, characterized in that when the α-C of the carboxyl in the carboxylic acid derivative is a chiral atom, the carboxylic acid derivative is in a single R configuration, in a single S configuration, or in both R and S configurations.

13. A compound that is selected from the group consisting of:
4-N,N-dimethylamino-2(R)-fluorobutyric acid hydrochloride;

4-N-isopropylamino-2(R,S)-fluorobutyric acid hydrochloride;
4-N,N-diethyl amino-2(R,S)-trifluoromethylbutyric acid hydrochloride;
4-N-benzylamino-2,2-difluorobutyric acid hydrochloride;
4-N-isobutylamino-2(R,S)-difluoromethylbutyric acid hydrochloride;
4-N-(aziridin-1-yl)-2(R,S)-difluoromethylbutyric acid hydrochloride;
4-N-(pyrrolidin-1-yl)-2(R,S)-fluorobutyric acid hydrochloride;
3-N-benzylamino-2(R,S)-(1,1-difluoromethyl)propionic acid hydrochloride;
6-N-cyclohexylamino-2(R,S)-trifluoromethylhexanoic acid hydrochloride;
4-benzyloxy-4-oxo-2(R,S)-fluorobutyric acid;
5-benzyloxy-5-oxo-2(R)-fluoropentanoic acid;
6-benzyloxy-6-oxo-2(S)-fluorohexanoic acid;
dibenzyl [1-(3-(R,S)-fluoro-3-carboxy)propyl] phosphate triester;
dibenzyl [1-(5-(S)-fluoro-5-carboxy)pentyl] phosphate triester;
4-(dibenzyloxy)phosphoryl-2(R,S)-fluorobutyric acid;
5-(dibenzyloxy)phosphoryl-2(R)-fluoropentanoic acid;
4-benzyloxy-4-oxo-2(R,S)-fluorobutyryl chloride;
sodium 5-benzyloxy-5-oxo-2(R)-fluorovalerate;
dibenzyl [1-(3-(R,S)-fluoro-4-oxo-4-chloro)butyl] phosphate triester;
dibenzyl [potassium 1-(4-(S)-fluoro-5-carboxylate)pentyl] phosphate triester;
4-(dibenzyloxy)phosphoryl-2(R,S)-fluorobutyryl chloride;
sodium 4-N,N-dimethylamino-2(R,S)-fluorobutyrate;
calcium 4-N,N-diethyl amino-2(R,S)-fluorobutyrate;
aluminum 3-N-b enzylamino-2(R,S)-benzyloxypropionate;
4-N,N-dimethylamino-2(R,S)-fluorobutyryl chloride hydrochloride;
4-N-benzylamino-2,2-difluorobutyryl chloride hydrochloride;
4-N,N-dimethylamino-2(R,S)-fluorobutyric acid; and
4-N,N-dimethylamino-2(S)-fluorobutyric acid hydrochloride.

* * * * *